US011504455B2

(12) United States Patent
Khapli et al.

(10) Patent No.: US 11,504,455 B2
(45) Date of Patent: Nov. 22, 2022

(54) FABRICATION OF NANOWIRES AND HIERARCHICALLY POROUS MATERIALS THROUGH SUPERCRITICAL $CO_2$ ASSISTED NEBULIZATION

(71) Applicant: NEW YORK UNIVERSITY, New York, NY (US)

(72) Inventors: Sachin Khapli, Abu Dhabi (AE); Ramesh Jagannathan, Abu Dhabi (AE)

(73) Assignee: New York University, New York, NY (US)

( * ) Notice: Subject to any disclaimer, the term of this patent is extended or adjusted under 35 U.S.C. 154(b) by 11 days.

(21) Appl. No.: 16/786,141

(22) Filed: Feb. 10, 2020

(65) Prior Publication Data

US 2020/0289717 A1 Sep. 17, 2020

Related U.S. Application Data

(63) Continuation of application No. 14/742,547, filed on Jun. 17, 2015, now abandoned.

(60) Provisional application No. 62/014,539, filed on Jun. 19, 2014.

(51) Int. Cl.
| | | |
|---|---|---|
| *A61L 31/08* | (2006.01) | |
| *A61L 31/02* | (2006.01) | |
| *A61L 31/16* | (2006.01) | |
| *A61L 31/14* | (2006.01) | |

(52) U.S. Cl.
CPC ........... *A61L 31/088* (2013.01); *A61L 31/022* (2013.01); *A61L 31/146* (2013.01); *A61L 31/16* (2013.01); *A61L 2400/12* (2013.01); *A61L 2420/02* (2013.01); *A61L 2430/02* (2013.01)

(58) Field of Classification Search
CPC .. A61K 2300/00; A61K 36/07; A61K 36/074; A61K 45/06; A61K 9/12; A61K 2800/10; A61K 2800/28; A61K 2800/413; A61K 8/0241; A61K 8/19; B82Y 10/00; B82Y 40/00; B82Y 30/00; C23C 14/024; C23C 14/048; C23C 14/228; C23C 16/047; C23C 16/45525; C23C 16/45555; A61L 2420/02; A61L 2430/02; A61L 31/022; A61L 31/088; A61L 31/146; A61L 31/16; A61L 2400/12
See application file for complete search history.

(56) References Cited

U.S. PATENT DOCUMENTS

| | | | |
|---|---|---|---|
| 5,639,441 A | 6/1997 | Sievers et al. | |
| 5,789,027 A * | 8/1998 | Watkins | B05D 1/18 |
| | | | 427/250 |
| 6,095,134 A | 8/2000 | Sievers et al. | |
| 6,630,121 B1 | 10/2003 | Sievers et al. | |
| 8,057,901 B2 * | 11/2011 | Ford | B82Y 40/00 |
| | | | 428/408 |
| 8,187,255 B2 * | 5/2012 | Weber | A61L 31/146 |
| | | | 604/890.1 |
| 2004/0137214 A1 * | 7/2004 | Chen | C30B 11/12 |
| | | | 428/323 |
| 2005/0220994 A1 * | 10/2005 | Mehta | B05D 1/025 |
| | | | 427/180 |

OTHER PUBLICATIONS

Sievers ("Formation of Aqueous Small Droplet Aerosols Assisted by Supercritical Carbon Dioxide", Aerosol Science and Technology, 30:1, 3-15, 1999, cited in parent application) (Year: 1999).*
Abdellah, et al., "Successive Spray Deposition of P3HT/PCBM Organic Photoactive Layers: Material Composition and Device Characteristics", Advanced Functional Materials, 2012, 22(19):4078-4086, abstract only.
Al-Hussein, M., et al., "In Situ X-ray Study of the Structural Evolution of Gold Nano-Domains by Spray Deposition on Thin Conductive P3HT Films", Langmuir, 2013, 29(8):2490-2497.
Askounis, et al., "Nanoparticle deposits near the contact line of pinned volatile droplets: size and shape revealed by atomic force microscopy", Soft Matter, 2011, 7(9):4152-4155.
Askounis, et al., "Structural transitions in a ring stain created at the contact line of evaporating nanosuspension sessile drops", Physical Review E, 2013, 87:012301, 8 pages.
Askounis, et al., "The effect of evaporation kinetics on nanoparticle structuring within contact line deposits of volatile drops", Colloids and Surfaces A: Physicochemical and Engineering Aspects, 2014, 441:855-866.
Baldwin, et al., "Drying and Deposition of Poly(ethylene Oxide) Droplets Determined by Peclet Number", Soft Matter, 2011, 7:7819-7826.
Bhardwaj, et al., "A numerical investigation on the influence of liquid properties and interfacial heat transfer during microdroplet deposition onto a glass substrate", International Journal of Heat and Mass Transfer, 2007, 50(15-16):2912-2923.

(Continued)

*Primary Examiner* — Audrea B Coniglio
(74) *Attorney, Agent, or Firm* — Foley & Lardner LLP

(57) ABSTRACT

A processing technique for creating nanowires and hierarchically porous micro/nano structures of ceramic materials is provided. The process includes evaporation of micron-sized water droplets containing dissolved organic salts on heated substrates followed by thermal decomposition of the deposited material. The micron-sized droplets may be generated by supercritical $CO_2$ assisted nebulization, in which high-pressure streams of aqueous solution and supercritical $CO_2$ are mixed, followed by controlled depressurization through a fine capillary. Rapid evaporation takes place on the heated substrates and structures are generated due to $CO_2$ effervescence from the droplets and evaporation of water, along with the pinning of the three phase contact line. Depending on the mass deposited, a mesh of nano-wires or membrane-like structures may result. Sintering of the membrane-like scaffolds above the decomposition temperature of the organic salt creates nanopores within the structures, creating a dual hierarchy of pores.

16 Claims, 16 Drawing Sheets

(56) References Cited

OTHER PUBLICATIONS

Bonfield, et al., "Designing porous scaffolds fortissue engineering", Philosophical Transactions of the Royal Society A, 2006, 364(1838):227-232.

Briones, et al., "A novel kinetically-controlled de-pinning model for evaporating water microdroplets", International Communications in Heat and Mass Transfer, 2012, 39(9):1311-1319.

Briones, et al., "Micrometer-Sized Water Droplet Impingement Dynamics and Evaporation on a Flat Dry Surface", Langmuir, 2010, 26(16):13272-13286.

Chae, et al., "Effect of Ordered Intermediate Porosity on Ion Transport in Hierarchically Nanoporous Electrodes", ACS Applied Materials & Interfaces, 2012, 4(8):3973-3979.

Chen, et al., "Hierarchically Oriented Macroporous Anode-Supported Solid Oxide Fuel Cell with Thin Ceria Electrolyte Film", ACS Applied Materials & Interfaces, 2014, 6(7):5130-5136.

Coelho, et al., "Basic research methods and current trends of dental implant surfaces", Journal of Biomedical Materials Research Part B: Applied Biomaterials, 2009, 88B(2):579-596.

Coelo & Jimbo, "Osseointegration of metallic devices: Current trends based on implant hardware design", Archives of Biochemistry and Biophysics, 2014, 561:99-108.

Coridan, et al., "Photoelectrochemical Behavior of Hierarchically Structured Si/WO3 Core-Shell Tandem Photoanodes", Nano Letters, 2014, 14(5):2310-2317.

Das, et al., "Dynamics of liquid droplets in an evaporating drop: liquid droplet 'coffee stain' effect", RSC Advances, 2012, 2(22):8390-8401.

Deegan, et al., "Contact line deposits in an evaporating drop", Physical Review E, 2000, 62(1):756-765.

Dunn, et al., "A mathematical model for the evaporation of a thin sessile liquid droplet: Comparison between experiment and theory", Colloids and Surfaces A: Physicochemical and Engineering Aspects, 2008, 323(1-3):50-55.

Dunn, et al., "The Effect of the Thermal Conductivity of the Substrate on Droplet Evaporation", Progress in Industrial Mathematics at ECMI, 2006, pp. 779-783.

Dunn, et al., "The strong influence of substrate conductivity on droplet evaporation", Journal of Fluid Mechanics, 2009, 623:329-351.

Duursma, et al., "Experimental Studies of Nanofluid Droplets in Spray Cooling", Heat Transfer Engineering, 2009, 30(13):1108-1120.

Fratzl, "Biomimetic materials research: what can we really learn from nature's structural materials?", Journal of the Royal Society Interface, 2007, 4(15):637-642.

Hanchak, et al., "One-dimensional models of nanoliter droplet evaporation from a hot surface in the transition regime", International Journal of Heat and Mass Transfer, 2013, 57(2):473-483.

He, et al., "Fabrication of Monodisperse Porous Zirconia Microspheres and Their Phosphorylation for Friedel-Crafts Alkylation of Indoles", ACS Applied Materials & Interfaces, 2014, 6(4):2718-2725.

Herzog, et al., "In Situ Grazing Incidence Small-Angle X-ray Scattering Investigation of Polystyrene Nanoparticle Spray Deposition onto Silicon", Langmuir, 2013, 29(36):11260-11266.

Hollister, "Porous scaffold design fortissue engineering", Nature Materials, 2005, 4:518-524.

Jeon, et al., "In Situ One-Step Synthesis of Hierarchical Nitrogen-Doped Porous Carbon for High-Performance Supercapacitors", ACS Applied Materials & Interfaces, 2014, 6(10):7214-7222.

Jimbo, et al., "The combined effects of undersized drilling and implant macrogeometry on bone healing around dental implants: an experimental study", International Journal of Oral and Maxillofacial Surgery, 2014, 43(10):1269-1275.

Jones, et al., "Hierarchical porous materials fortissue engineering", Philosophical Transactions of the Royal Society A, 2006, 364(1838):263-281.

Koch, et al., "Accelerated evaporation of microdroplets at ambient conditions for the on-line analysis of nanoparticles by inductively-coupled plasma mass spectrometry", Journal of Analytical Atomic Spectrometry, 2013, 28(11):1707-1717.

Krogman, et al., "Spraying asymmetry into functional membranes layer-by-layer", Nature Materials, 2009, 8:512-518.

Lim, et al., "Evaporation of inkjet printed pico-liter droplet on heated substrates with different thermal conductivity", Journal of Mechanical Science and Technology, 2009, 23(7):1788-1794.

Liu, et al., "Incorporation of growth factors into medical devices via biomimetic coatings", Philosophical Transactions of the Royal Society A, 2006, 364(1838):233-248.

Lu, et al., "MOF-Templated Synthesis of Porous Co3O4 Concave Nanocubes with High Specific Surface Area and Their Gas Sensing Properties", ACS Applied Materials & Interfaces, 2014, 6(6):4186-4195.

Luckarift, et al., "Facile Fabrication of Scalable, Hierarchically Structured Polymer/Carbon Architectures for Bioelectrodes", ACS Applied Materials & Interfaces, 2012, 4(4):2082-2087.

Orejon, et al., "Stick-Slip of Evaporating Droplets: Substrate Hydrophobicity and Nanoparticle Concentration", Langmuir, 2011, 27(21):12834-12843.

Pan, et al., "Assessment of Water Droplet Evaporation Mechanisms on Hydrophobic and Superhydrophobic Substrates", Langmuir, 2013, 29(51):15831-15841.

Pinto, et al., "Block Copolymers Self-Assembly Allows Obtaining Tunable Micro or Nanoporous Membranes or Depth Filters Based on PMMA; Fabrication Method and Nanostructures", The Journal of Physical Chemistry C, 2014, 118(9):4656-4663.

Putnam, et al., "Interfacial heat transfer during microdroplet evaporation on a laser heated surface", International Journal of Heat and Mass Transfer, 2012, 55(23-24):6307-6320.

Putnam, et al., "Microdroplet evaporation on superheated surfaces", International Journal of Heat and Mass Transfer, 2012, 55(21-22):5793-5807.

Putnam, et al., "Role of entrapped vapor bubbles during microdroplet evaporation", Applied Physics Letters, 2012, 101(7):071602, 4 pages.

Sai, et al., "Hierarchical Porous Polymer Scaffolds from Block Copolymers", Science, 2013, 341(6145):530-534.

Sakar, K., et al., "Monitoring Structural Dynamics of In situ Spray-Deposited Zinc Oxide Films for Application in Dye-Sensitized Solar Cells", ChemSusChem, 2014, 7(8):2140-2145.

Sefiane, "On the Formation of Regular Patterns from Drying Droplets and Their Potential Use for Bio-Medical Applications", Journal of Bionic Engineering, 2010, 7:S82-S93.

Sefiane, "Patterns from drying drops", Advances in Colloid and Interface Science, 2014, 206:372-381.

Semenov, et al., "Computer Simulations of Evaporation of Pinned Sessile Droplets: Influence of Kinetic Effects", Langmuir, 2012, 28(43):15203-15211.

Semenov, et al., "Droplets evaporation: Problems and solutions", The European Physical Journal Special Topics, 2011, 197:265-278.

Semenov, et al., "Evaporation of pinned sessile microdroplets of water on a highly heat-conductive substrate: Computer simulations", The European Physical Journal Special Topics, 2013, 219(1):143-154.

Semenov, et al., "Evaporation of sessile water droplets: Universal behaviour in presence of contact angle hysteresis", Colloids and Surfaces A: Physicochemical and Engineering Aspects, 2011, 391 (1-3): 135-144.

Sievers, "Formation of Aqueous Small Droplet Aerosols Assisted by Supercritical Carbon Dioxide", Aerosol Science and Technology, 1999, 30(1):3-15.

Sievers, et al., "Micronization of water-soluble or alcohol-soluble pharmaceuticals and model compounds with a low-temperature Bubble Dryer", The Journal of Supercritical Fluids, 2003, 26(1):9-16.

Sobac, B., et al., "Thermal effects of the substrate on water droplet evaporation", Physical Review E, 2012, 86:021602, 10 pages.

Sohn, et al., "Porous Spherical Carbon/Sulfur Nanocomposites by Aerosol-Assisted Synthesis: The Effect of Pore Structure and Morphology on Their Electrochemical Performance As Lithium/Sulfur Battery Cathodes", ACS Applied Materials & Interfaces, 2014, 6(10):7596-7606.

(56) References Cited

OTHER PUBLICATIONS

Su, et al., "Insights into Hierarchically Structured Porous Materials: From Nanoscience to Catalysis, Separation, Optics, Energy, and Life Science", Hierarchically Structured Porous Materials, 2012, pp. 3-27.

Sui, et al., "Preparation of Three-Dimensional Graphene Oxide-Polyethylenimine Porous Materials as Dye and Gas Adsorbents", ACS Applied Materials & Interfaces, 2013, 5(18):9172-9179.

Tian, et al., "Hierarchically Structured ZnO Nanorods-Nanosheets for Improved Quantum-Dot-Sensitized Solar Cells", ACS Applied Materials & Interfaces, 2014, 6(6):4466-4472.

Wang, et al., "Synthesis of Nestlike ZnO Hierarchically Porous Structures and Analysis of Their Gas Sensing Properties", ACS Applied Materials & Interfaces, 2012, 4(2):817-825.

Wiebe, R., et al., "The Solubility of Carbon Dioxide in Water at Various Temperatures from 12 to 40 and at Pressures to 500 Atmospheres. Critical Phenomena*", Journal of the American Chemical Society, 1940, 62(4):815-817.

Xu, Z., et al., "Graphene chiral liquid crystals and macroscopic assembled fibres," Nature Communications, 2011, 2:571, 9 pages.

Xu, W., et al., "Evaporation Kinetics of Sessile Water Droplets on Micropillared Superhydrophobic Surfaces", Langmuir, 2013, 29(20):6032-6041.

Yu, et al., "A Tin-Based Amorphous Oxide Composite with a Porous, Spherical, Multideck-Cage Morphology as a Highly Reversible Anode Material for Lithium-Ion Batteries", Advanced Materials, 2007, 19(7):993-997.

Zhang, et al., "Hierarchically Porous ZnO Architectures for Gas Sensor Application", Crystal Growth & Design, 2009, 9(8):3532-3537.

Zhu, et al., "Facile Fabrication and Enhanced Sensing Properties of Hierarchically Porous CuO Architectures", ACS Applied Materials & Interfaces, 2012, 4(2):744-751.

Zhu, et al., "Facile Fabrication of Hierarchically Porous $CuFe_2O_4$ Nanospheres with Enhanced Capacitance Property", ACS Applied Materials & Interfaces, 2013, 5(13):6030-6037.

Zhu, et al., "Synthesis of Silver Nanoparticles Confined in Hierarchically Porous Monolithic Silica: A New Function in Aromatic Hydrocarbon Separations", ACS Applied Materials & Interfaces, 2013, 5(6): 2118-2125.

Non-Final Office Action in U.S. Appl. No. 14/742,547, filed Jun. 30, 2016, 13 pages.

* cited by examiner

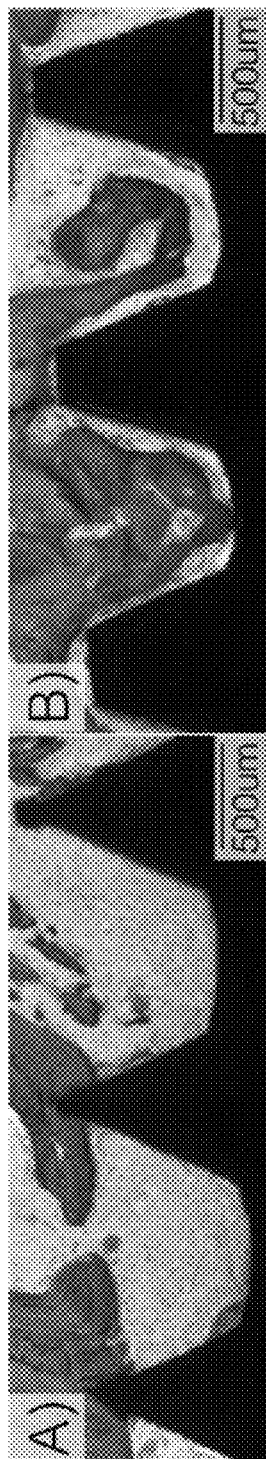
Figures 14(a)
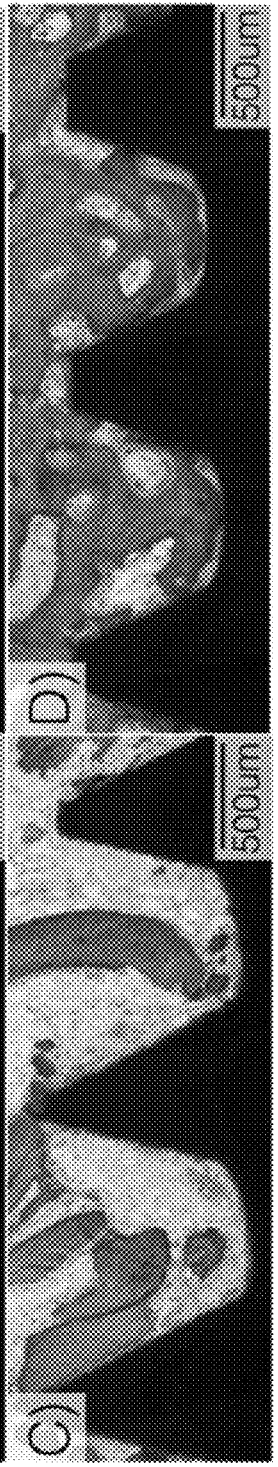
Figures 14(b)
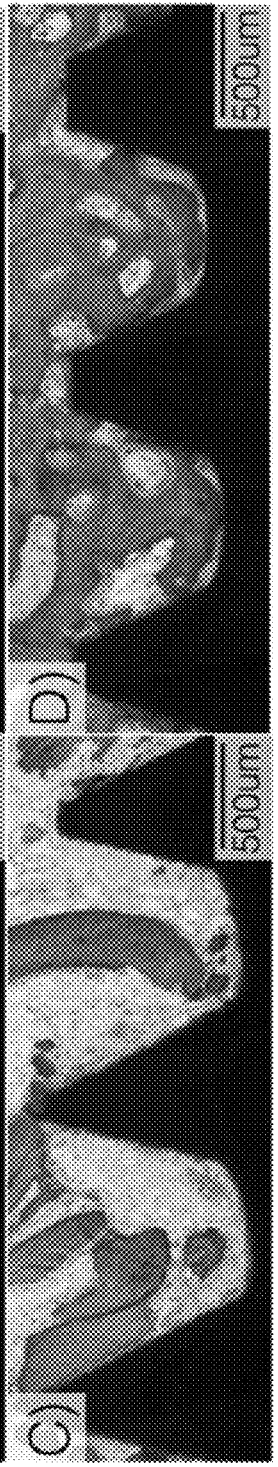
Figures 14(c)
Figures 14(d)
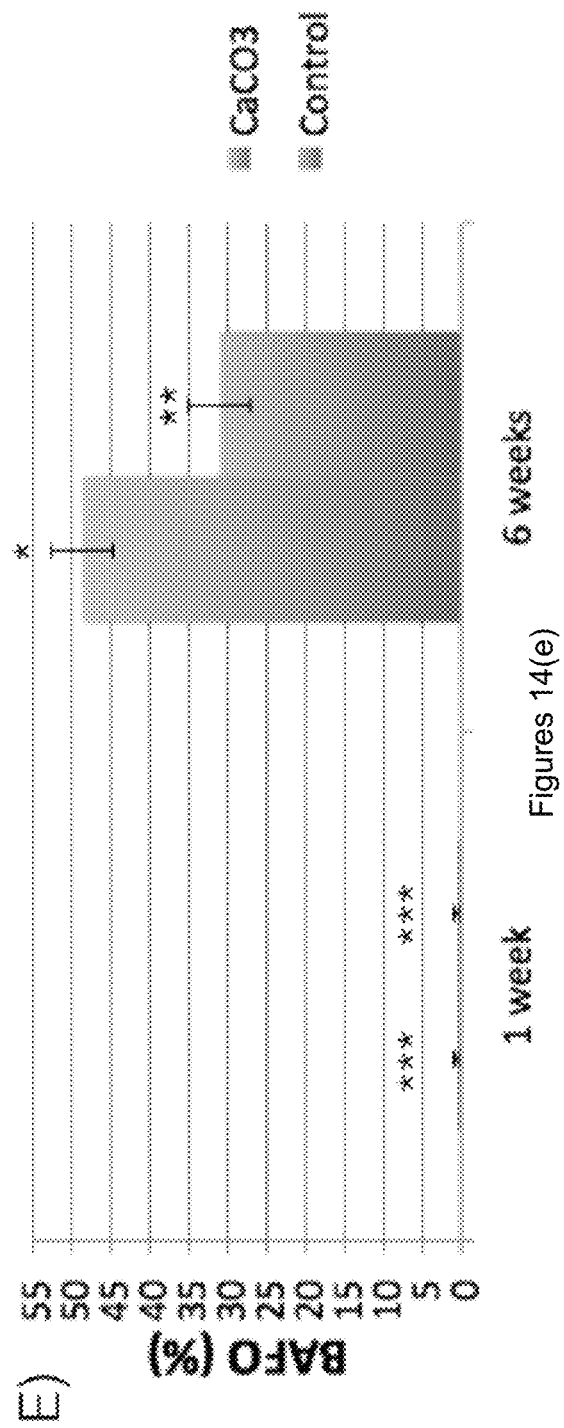
Figures 14(e)

FABRICATION OF NANOWIRES AND HIERARCHICALLY POROUS MATERIALS THROUGH SUPERCRITICAL CO₂ ASSISTED NEBULIZATION

CROSS-REFERENCE TO RELATED APPLICATIONS

This application is a continuation of U.S. patent application Ser. No. 14/742,547 filed Jun. 17, 2015, which claims the benefit of priority to U.S. Provisional Application No. 62/014,539 filed Jun. 19, 2014, both of which are hereby incorporated by reference in their entirety.

BACKGROUND

Porous materials with structural hierarchy are abundant in nature, for example, diatom skeletons, butterfly wings, corals, sponge, wood, and bone all exhibit structural hierarchy. These materials are composed of structural elements that are themselves structured on finer scales, yielding an overall organization of matter on the macro, micro, and nano scales that results in exceptional functional properties. Bone, for example, possesses seven layers of hierarchical structure and this structure is responsible for its exceptional mechanical properties.

Hierarchically structured porous materials have numerous applications across a broad range of technologies. Due to selective permeation, these materials may be useful in adsorption, separation, and purification of gases and liquids. The combination of the large surface area and selective permeability of these materials may offer unique advantages in catalysis. Highly ordered 3D microstructures may be useful in optics applications such as lasing, waveguides, photonic band gap materials, and sensors. In the field of energy generation and storage, these materials may provide more efficient solar cells, fuel cells, electrode materials, and supercapacitors. In the life sciences, these materials may be useful as biocompatible scaffolds for promoting cell adhesion and also in drug delivery applications.

There has been considerable research devoted towards the fabrication of artificial materials that mimic the hierarchically structured porous materials observed in nature. Most of the preexisting fabrication techniques utilize sacrificial templates such as colloidal crystals, emulsions, salts, ice crystals, gas bubbles, supramolecular aggregates, and biomaterials to form a hierarchical structure. Bottom up approaches based on self-assembly have also been applied for fabrication of porous polymeric materials. Scalability and control over pore size are challenges associated with the preexisting processes.

SUMMARY

A process for the formation of nanowires and hierarchically porous materials is provided. The process may include mixing a stream of supercritical $CO_2$ with an aqueous solution of an organic salt in a continuous flow operation, creating an aerosol from the mixture, and depositing the aerosol on heated substrates. The process may additionally include sintering the deposited material. The sintering may produce a nanowire mesh or a hierarchically porous structure, and may occur at a temperature of at least about 300° C. for about 6 hours to about 8 hours. The supercritical $CO_2$ may be at a pressure of about 0.1 MPa to about 0.3 MPa. The creation of the aerosol may include rapidly expanding the mixture through a capillary, nozzle, or tube. The heated substrate may be at a temperature of about 80° C. to about 150° C. The organic salt may be described by the formula:

wherein M is at least one of Ca, Ag, Cu, Zn, Co, Fe, Mn, and Ni, and N is at least one of acetate ($CH_3COO^-$), acetylacetonate ($CH_3COCH_2COO^-$), oxalate ($C_2O_4^{2-}$), and hydroxide ($OH^-$). The deposited material may include nanowires, microporous inorganic membranes, or nanopores with an average diameter of less than about 100 nm and pores with an average diameter of greater than about 100 nm. The deposited material may have a thickness of less than about 100 nm or of about 1 µm to about 3 The deposited material may include $CaCO_3$. The substrate may include titanium, and may be a medical implant.

A process for the formation of nanowires and hierarchically porous materials is provided. The process may include creating an aerosol from an aqueous solution of an organic salt in a continuous flow operation, and depositing the aerosol on heated substrates. The aerosol is created by an inkjet process.

A composite medical implant is provided. The composite medical implant includes a medical implant substrate and a coating disposed on a surface of the medical implant substrate. The coating is biocompatible and osseoconductive. The coating includes a nanowire mesh or a hierarchically porous structure. The medical implant substrate may include titanium. The coating may include $CaCO_3$.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 14(a)-(d) are optical micrographs of implant in bone slices—FIG. 14(a) uncoated implant after 1 week in vivo, FIG. 14(b) implant with $CaCO_3$ coating after 1 week in vivo, FIG. 14(c) uncoated implant after 6 weeks in vivo, FIG. 14(d) implant with $CaCO_3$ coating after 6 weeks in vivo, and FIG. 14(e) is a statistical analysis of Bone Area Fraction Occupancy (BAFO) for each implant with the number of asterisks indicating statistically homogeneous groups.

DETAILED DESCRIPTION

Figure 1A:
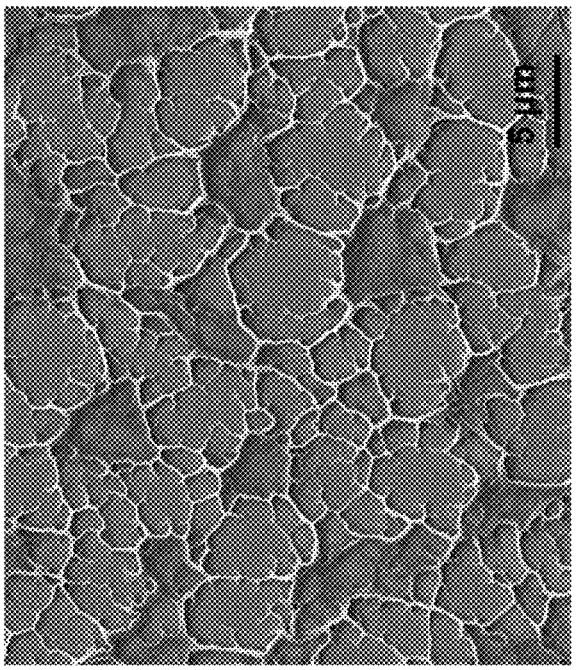
FIGS. 1(a)-(d) are images of morphologies of $CaCO_3$ structures obtained by an aerosol deposition process at a temperature of 130° C. and various pressures (P) including P=126 bar, P=137 bar, P=80 bar, and P=120 bar, respectively.
Figure 1B:
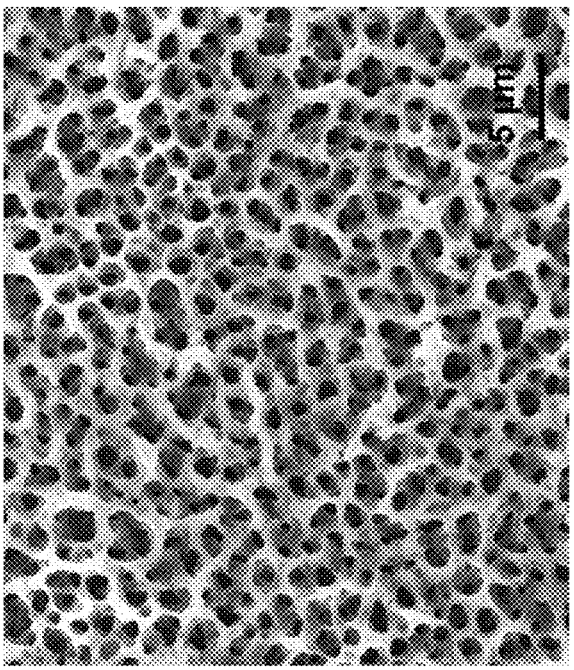
Figure 1C:
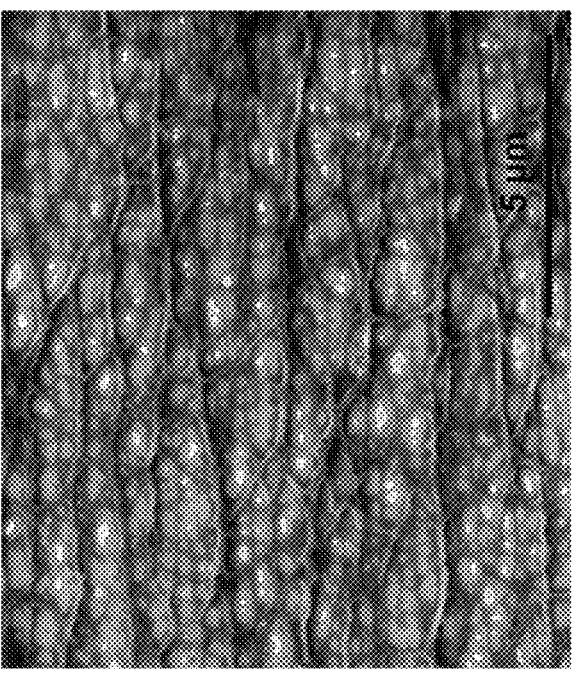
Figure 1D:
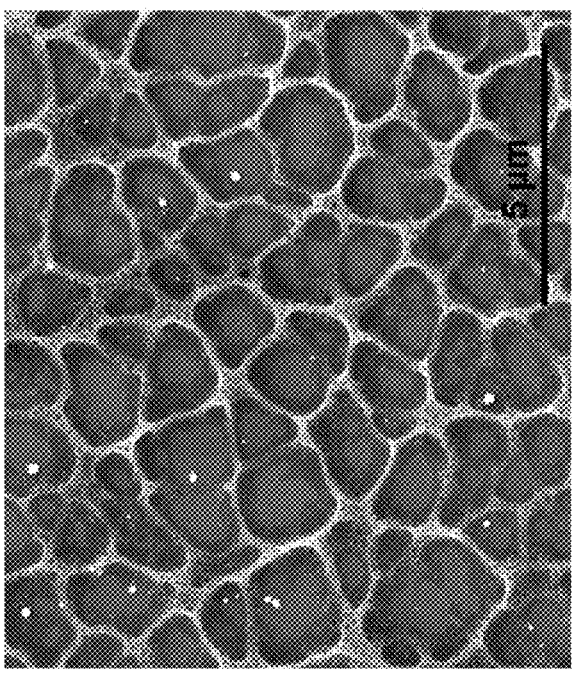

Following below are more detailed descriptions of various concepts related to, and embodiments of, inventive processes for the formation of nanowires and hierarchically porous materials. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A method for the fabrication of hierarchically porous materials through the phenomenon of coffee-ring effect is provided. The coffee-ring effect refers to the formation of ring like patterns during the evaporation of liquid droplets. The pinning of the three phase contact line may produce substantial material deposition at the boundary of the evaporating droplet, which leads to the formation of circular patterns after drying. This phenomenon has been studied for a variety of liquids, solutes/dispersants, surfaces, and droplet sizes. A mathematical model for understanding the formation of circular patterns after evaporation has been developed. Experimental and numerical investigations of microdroplet drying phenomena have been investigated in terms of heat and mass transfer, such as the heat transport during evaporation of droplets on various substrates and the thermal effects during evaporation of microdroplets with a radius of about 85 μm on a variety of surfaces and across surface temperatures in the range of 25-250° C. The phenomena of the coffee-ring effect has been utilized for the deposition of colloidal particles using single drops of millimeter size. Herein, the coffee-ring effect has been extended to the evaporation of microdroplets from a dense aerosol, producing hierarchically porous materials including 2D and 3D patterns. By contrast, preexisting spray coating methods have generally been developed to obtain continuous films.

A supercritical carbon dioxide (sc-$CO_2$) based nebulization process is employed in the fabrication of hierarchically porous materials. The process may include the dissolution of $CO_2$ in water, and a subsequent de-pressurization creating dense aerosols with droplet sizes of less than about 3 μm. Along with the small size of the droplets produced, this method offers the additional advantage of the aerosol droplets being saturated with carbon dioxide. The saturation with $CO_2$ may allow the production of "inorganic foam" like porous microstructures. A subsequent drying of the aerosol in a bubble dryer may yield sub-micron sized particles. This process may be employed for the generation of micron sized water droplets containing dissolved salts for deposition. The fabrication method of hierarchically porous materials may not employ any sacrificial templates in the creation of 3D scaffolds of ceramics, and is applicable to a wide variety of materials. The fabrication process is scalable, and the use of supercritical $CO_2$ as a medium for the synthesis is environmentally friendly.

A process for sc-$CO_2$ assisted nebulization may be a continuous flow process, in which a stream of sc-$CO_2$ is mixed with an aqueous stream containing the solute of interest, and the mixture is allowed to expand at atmospheric pressure after passing through a heat exchanger. Upon mixing in a low-dead-volume mixing tee, the $CO_2$ dissolves in the aqueous phase at high pressure. $CO_2$ solubility in water is 2.2 mole percent at 40° C. and 100 bar. According to one embodiment, the sc-$CO_2$ pressure may be about 0.1 MPa to about 0.3 MPa.

The solute of interest may be an organic salt. The organic salt may be described by the formula:

$$M_x(N)_y,$$

wherein M is at least one of Ca, Ag, Cu, Zn, Co, Fe, Mn, and Ni; N is at least one of acetate ($CH_3COO^-$), acetylacetonate ($CH_3COCH_2COO^-$), oxalate ($C_2O_4^{2-}$), and hydroxide (OH); x is 1 to 4; and y is 1 to 4. The aqueous stream may include more than one organic salt. The solute may include water soluble inorganic pre-cursors.

An aerosol may be generated during depressurization of the aqueous stream in a two-step process. In the first step, the undissolved sc-$CO_2$ phase may expand to gaseous $CO_2$ and create a dispersion of aqueous droplets that are supersaturated with $CO_2$. In the second step, the aqueous droplets may undergo further breakdown due to a rapid release of the dissolved $CO_2$ gas, and produce a fine aerosol with a particle size of about 0.1 μm to about 3 μm. The aerosol may then be directed onto heated substrates, producing rapid effervescence of $CO_2$ as well as evaporation of the microdroplets to generate microstructures. The type of microstructures generated may depend on the deposition time.

The microstructures may be further sintered at about 300° C. to about 450° C. to induce decomposition of the remaining organic salts and create nanopores within the walls of the microstructures. The sintered microstructures may include a dual hierarchy of pores, such as nanopores and pores with an average diameter greater than about 100 nm. The dual hierarchy of pores may refer to a material with a bimodal pore diameter distribution. As utilized herein, nanopores may refer to pores with a diameter of less about 100 nm. The larger pores contained in the deposited structure may have a diameter of about 2 µm to about 4 µm.

The overall process of formation of the microstructures may be influenced by the following parameters: the pressure of the $CO_2$ stream, the droplet size, the number density of the aerosol, concentration and nature of the solute dissolved, wettability of the substrate, thermal conductivity of the substrate, temperature of the heated substrate, and the deposition time. FIGS. 1(a)-(d) show the various morphologies observed for calcium carbonate ($CaCO_3$) deposition under different conditions. FIGS. 2(a)-(d) show the morphologies observed for the deposition of cobalt oxide, copper oxide, cobalt doped zinc oxide, and silver oxide, respectively. The amount of material deposited produces different morphologies, ranging from a network of nanowires (2-D) to thin and thick porous scaffolds (3-D). The morphologies observed are, generally speaking, similar across the selected the materials, with some minor differences depending on the decomposition properties of deposited materials.

The influence of various process parameters on the deposited microstructures was studied. The understanding of the manner in which the process parameters affect the produced microstructures allows effective control of the process. Qualitative results were produced utilizing calcium acetate as a precursor, and similar experiments were conducted for other materials as well. The structures produced by the process may include at least one of $CaCO_3$, $ZnO$, $CuO$, $Co_3O_4$, Co-doped $ZnO$, $Ag_2O$, $Fe_3O_4$, $MnO$, and $NiO$.

The structures produced may include biocompatible materials. The biocompatible materials may form biocompatible scaffolds that promote cell adhesion. Additionally, the biocompatible materials may release ions, such as bioactive ceramic ions, that facilitate increased healing rates. The structures may also be osseoconductive. An exemplary structure that is both biocompatible and osseoconductive may include $CaCO_3$. Structures that are biocompatible may be utilized in vivo. The biocompatible structures may be formed on substrates that include medical implants. The medical implants may include any biocompatible material with the appropriate mechanical properties, such as titanium or stainless steel. The medical implants may have any appropriate form, such as dental implants, screws, plates, mesh, rods, or joint replacement components. The biocompatible structures may be disposed over a portion of the medical implant surface, or in some cases over the entirety of the medical implant surface.

The effect of $CO_2$ pressure on the aerosol dynamics and the formation of microstructures was investigated. The $CO_2$ pressure affects the solubility of $CO_2$ in water, the flow dynamics of the aerosols produced, and the amount of Joule-Thomson cooling that accompanies the expansion. The solubility of $CO_2$ in water is directly proportional to the pressure, as described by Henry's law, whereas the flow dynamics of the aerosol may also be affected by the geometry of expansion. For a given flow geometry, the Joule-Thomson effect may limit the operating pressure to a value above which there is significant condensation of dry ice in the flow.

Various geometries of expansion were explored, including a 125 µm diameter nozzle orifice with an aspect ratio of 5, a 125 µm diameter capillary tube with a length of 1 inch and aspect ratio of 203, and a 1/16 inch diameter stainless steel tube with a length of 2 inches and an aspect ratio of 32. It was observed that pressures up to about 300 bar may be realized using either the nozzle or the capillary tube, however there was significant Joule-Thomson cooling. The Joule-Thomson cooling produced the condensation of dry ice and caused an intermittent flow in the absence of sufficient external heating. The maximum pressure attainable using the 1/16 inch diameter tube was 137 bar, however the flow was largely unaffected by Joule-Thomson cooling.

The morphologies of microstructures obtained using the different flow geometries were largely similar despite the mass flow rates of the aerosols being significantly different. The large 1/16 inch diameter stainless steel tube produced aerosols with higher mass flow rates and required shorter exposure times for the deposition of similar amounts of material. Unless otherwise specified, experiments were conducted using the 1/16 inch diameter stainless steel tube for expansion.

Figure 3B:
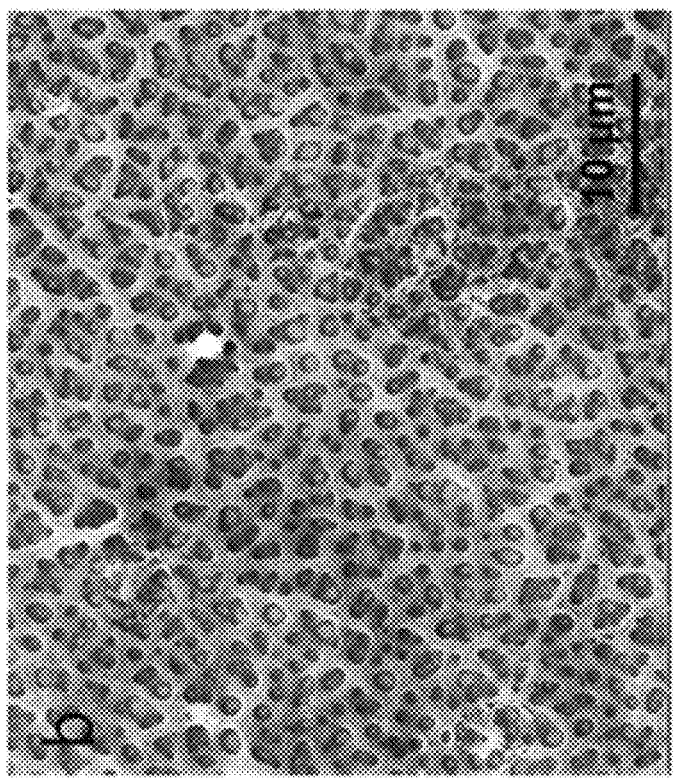
FIGS. 3(a) and 3(b) are images of morphologies of $CaCO_3$ structures produced at a $CO_2$ pressure of 80 bar and 100 bar, respectively.
Figure 3A:
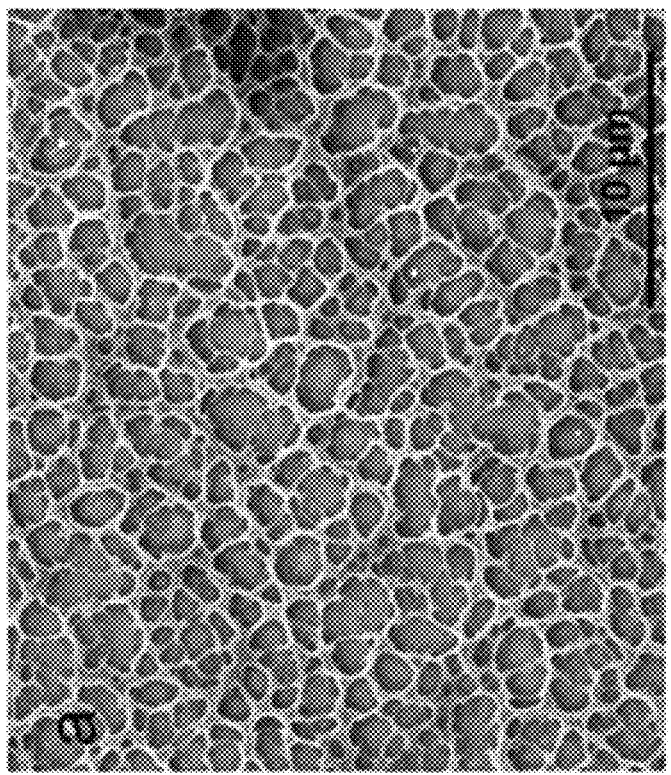

FIGS. 3(a) and 3(b) show the morphology of $CaCO_3$ microstructures formed at $CO_2$ pressures of 80 bar and 100 bar, respectively. The pore size produced at each pressure, of about 1 µm to about 2 µm, is similar, however the pore walls are broader at low pressure for equivalent deposition times. Based on the outcomes of the pressure experiments a $CO_2$ pressure of 120 bar was selected as the operating pressure. The $CO_2$ pressure may also affect the pH and ionic equilibrium of the droplets.

Figure 4A:
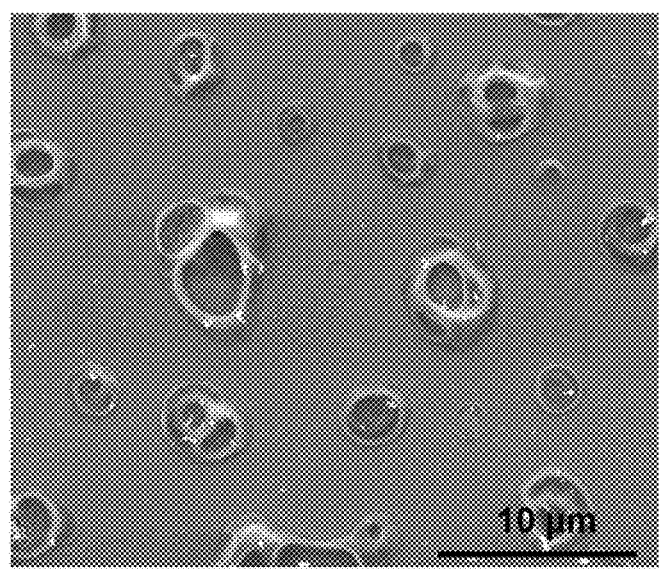
FIGS. 4(a)-(c) are images of the morphology of deposited structures produced at temperatures of 80° C., 130° C. and 150° C., respectively.
Figure 4B:
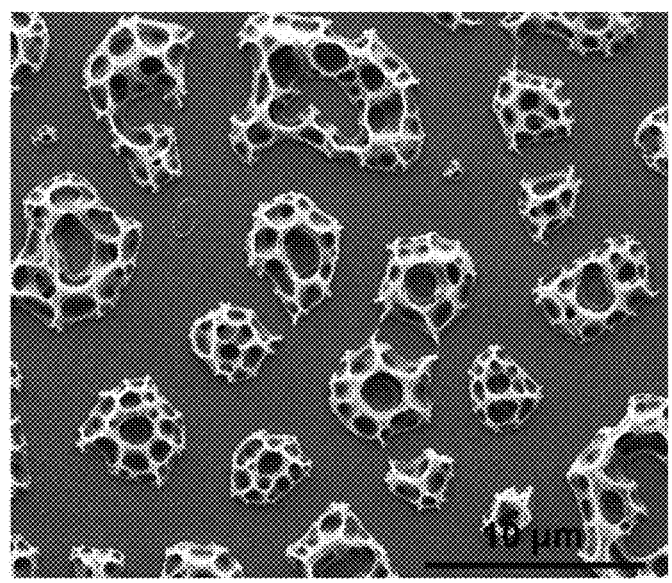
Figure 4C:
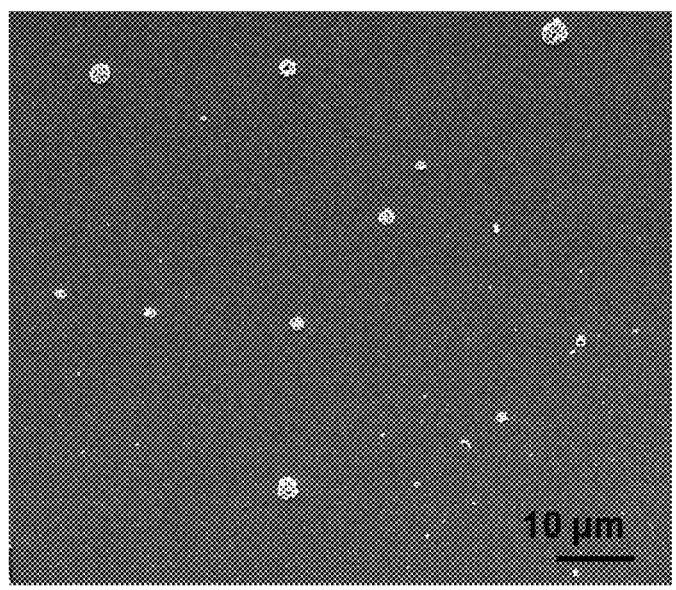

The effect of surface temperature on the morphology of the microstructures was investigated while maintaining a constant operating pressure. Films were deposited at different surface temperatures and were observed under FE-SEM after sintering at 300° C. to 450° C. FIGS. 4(a)-(c) show different patterns of dried droplets at substrate temperatures of 80° C., 130° C. and 150° C., respectively. Aerosol droplets collected on a surface at a temperature of 80° C. produce drying patterns consistent with single droplet drying events as well as coalescence of droplets, either on the surface or in-flight, as shown in FIG. 4(a). At a surface temperature of 130° C., similar deposition patterns were obtained, however the number of pores formed was greater and the average pore size was smaller as shown in FIG. 4(b). In the temperature range of about 80° C. to about 130° C., the morphologies of dried droplets may be similar to the morphologies observed for aerosol droplets drying in flight. Deposition at substrate temperatures above about 150° C. may yield nearly spherical particles that are smaller in size and have different pore structures. For example, FIG. 4(c) shows that a deposition on a surface at a temperature of 150° C. resulted in only a small amount of material being deposited on the surface.

The Weber numbers for the aerosol droplets are given by the formula:

$$W_e = \frac{\rho V_{im}^2 D_{im}}{\gamma},$$

wherein $V_{im}$ is the droplet impact velocity, $D_{im}$ is the droplet diameter, $\rho$ is the density of the fluid and $\gamma$ is the surface tension of the droplets. The Weber numbers for the aerosol droplets impinging on the heated surfaces wherein 3 µm≤$D_{im}$≤6 µm and 0.5 m/s≤$V_{im}$≤3 m/s are small enough ($W_e$≥0.1) such that the phenomena of droplet recoil, jetting, splash, break-up and rebound do not occur during the deposition process. As a result, the droplets stick to the surface upon impact and evaporation occurs.

Preexisting spray-coating processes are generally designed to create thin, continuous films without any voids. The aerosol deposition process described herein produces a porous microstructure. Mechanistic understanding of the process of microstructure-formation can be developed through the interpretation of the effects of various process parameters on the final microstructure. Based on previous investigations of microdroplets with a diameter of 30-85 μm across a temperature range 25-250° C., the evaporation rate is initially constant for about half the lifetime of the droplet, after which stick-slip contact angle dynamics take place. Across the droplet diameter range of about 30 μm to a few millimeters initial evaporation rate scales linearly with the contact radius, surface temperature, and substrate thermal conductivity. Droplet lifetime in the diameter range of about 30 μm to about 85 μm may be on the order of 100 ms, and may decrease with droplet size. Droplet lifetimes for 17 μm diameter droplets of about 10 ms at 110° C. have been reported. Droplet lifetimes with a similar order of magnitude may be produced due to the evaporation of aerosol droplets on heated substrates as employed in the process described herein.

The evaporation of the aerosol droplets is complicated by the fact that the droplets are saturated with $CO_2$ gas when they strike the surface. $CO_2$ has a high solubility in water at room temperature (20° C.) and pressure (1 bar) of 0.9 $cm^3$/g, and the release of $CO_2$ during aerosol formation is not sufficient to exhaust the $CO_2$ contained in the liquid such that the formed aerosol droplets are saturated with $CO_2$ gas. The solubility of $CO_2$ in water decreases rapidly with rising temperature. Therefore, bubble formation is highly likely to occur when the aerosol droplet strikes the heated surface. The effervescence of $CO_2$ has a lower activation energy than the evaporation of the droplet liquid, and therefore should take place at a much faster rate than the evaporation. The solubility data indicates that bubbles with diameters of about 1 μm to about 1.5 μm may form within a 3 μm diameter droplet when heated from 20° C. to 80° C. The formation of bubbles within the drying droplets at a temperature below the saturation temperature of water at 1 bar is evident in the microstructure shown in FIG. 4(a). The collapse of the entrapped bubbles in the droplets on the heated surface leads to the formation of coffee-rings. The trapped bubbles may be formed even below the saturation temperature due to the dissolved $CO_2$, and may significantly enhance the coffee-ring effect which is shown in FIGS. 4(a) and 4(b). Another indication for the role of $CO_2$ effervescence in shaping the drying patterns is provided in FIG. 4(c), where the collapse of drying bubbles in flight, before the deposition on the heated surface, indicates that a thin vapor layer is formed. The formation of the thin vapor layer may be similar to the Leidenfrost effect, despite the fact that the temperature is far below the Leidenfrost temperature of pure water of 190° C. to 200° C. For microdroplet evaporation on Cu surfaces, maximum evaporative heat fluxes may be observed quickly at low superheats of (10° C.≤ΔT≤25° C.). The formation of drying patterns at superheats of similar orders of magnitudes are observed in the process described herein.

Figure 2A:
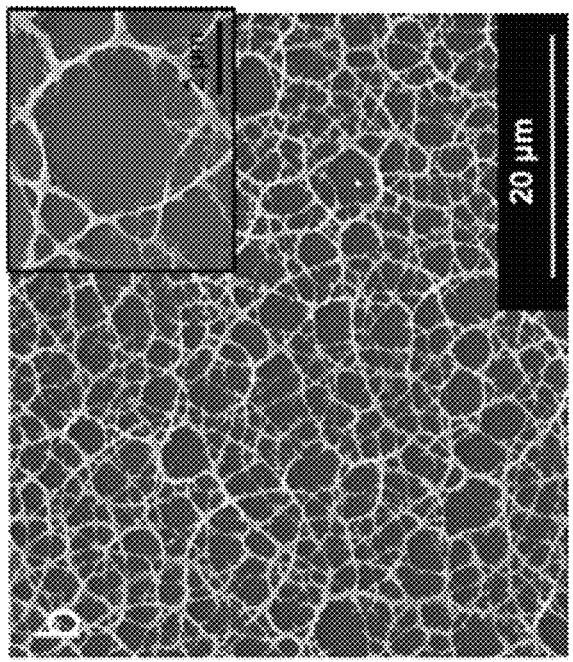
FIGS. 2(a)-(d) are images of the morphologies of porous structures obtained from an aerosol deposition process for various materials—FIG. 2(a) cobalt oxide, FIG. 2(b) copper oxide, FIG. 2(c) cobalt doped zinc oxide, and FIG. 2(d) silver oxide.
Figure 2B:
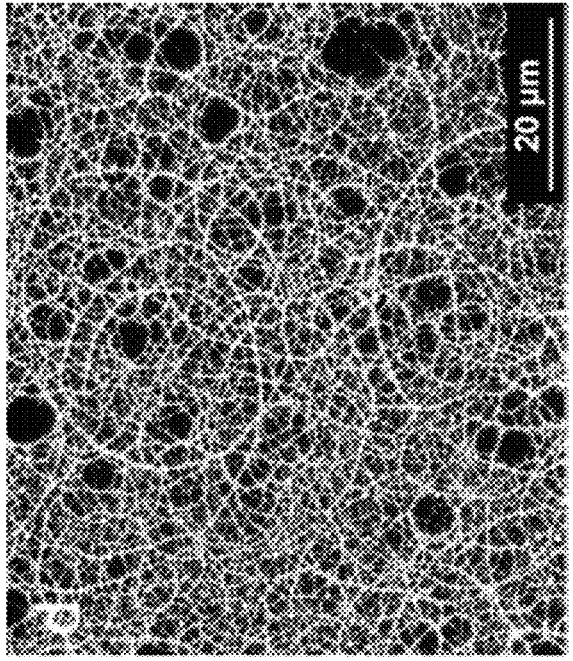
Figure 2C:
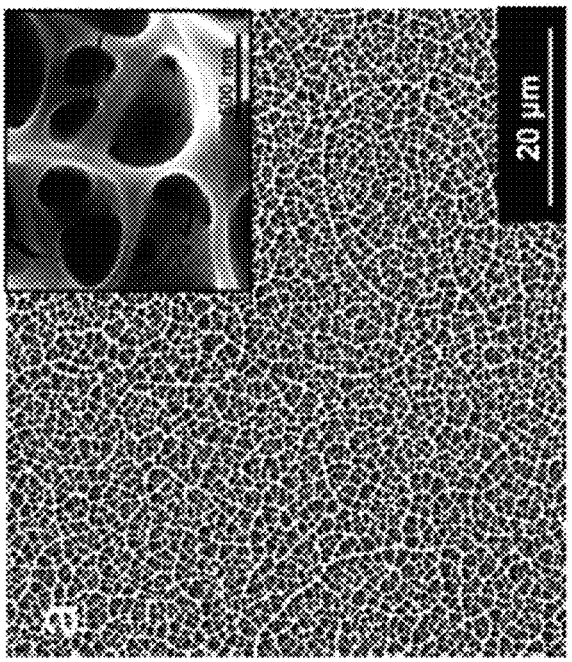
Figure 2D:
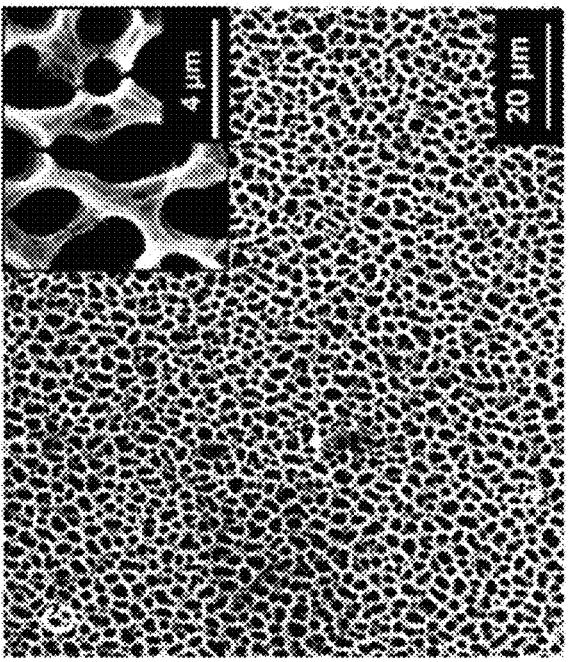
Figure 5:
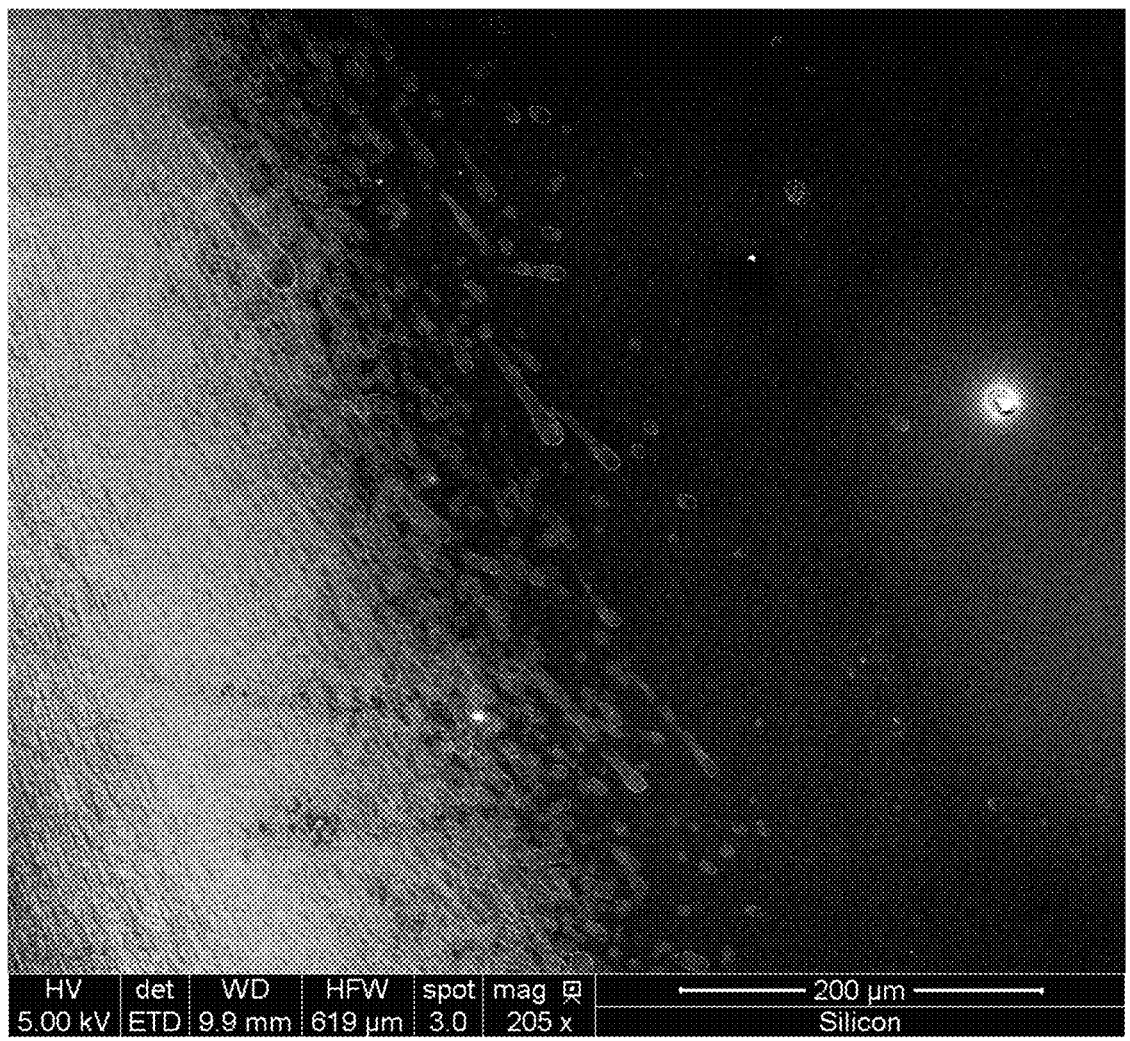
FIG. 5 is a deposition pattern in a shadowed region with a low probability of droplet impact.
Figure 6:
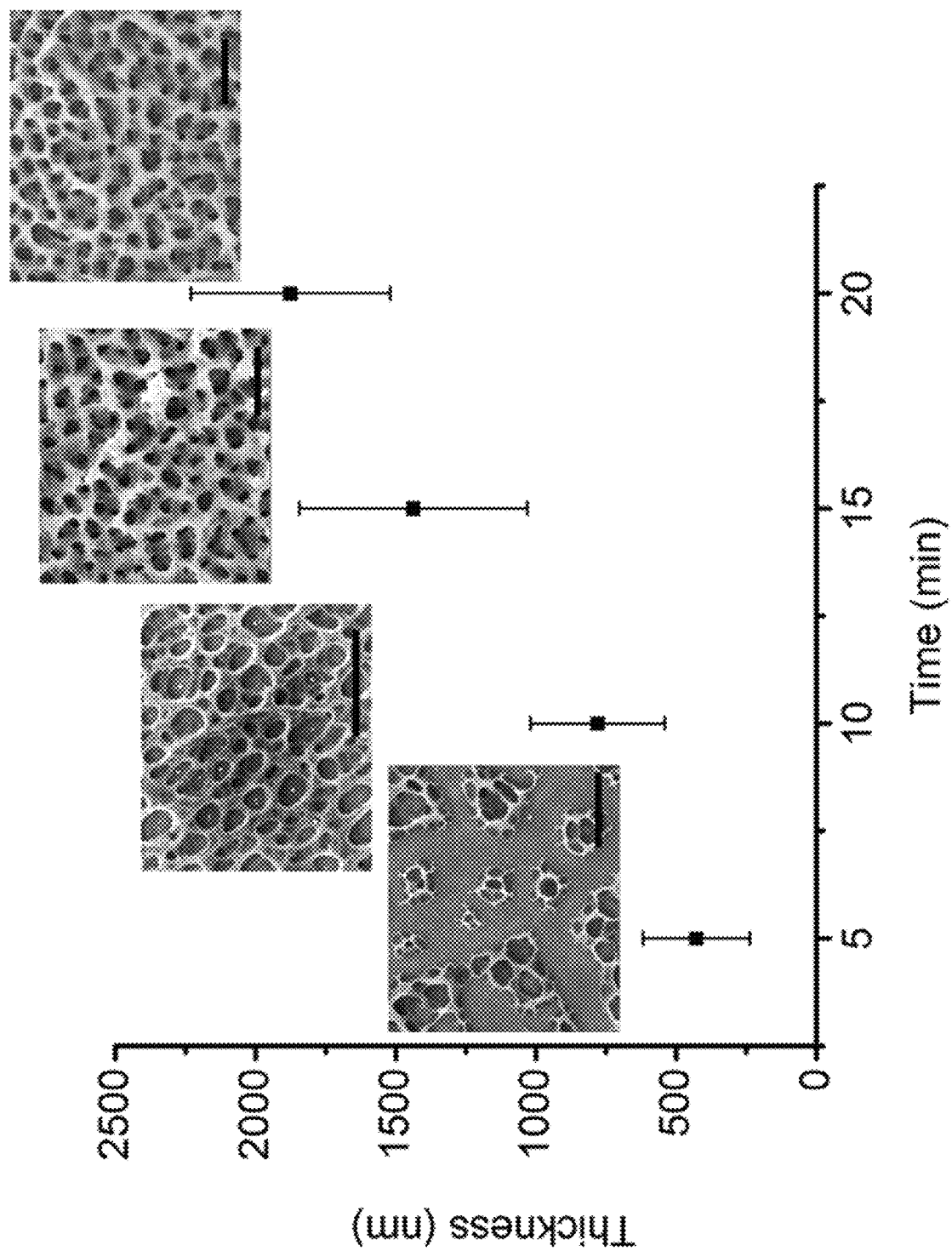
FIG. 6 depicts the deposited film thickness as a function of deposition time at a temperature of 130° C. and a $CO_2$ pressure of 120 bar.
Figure 7A:
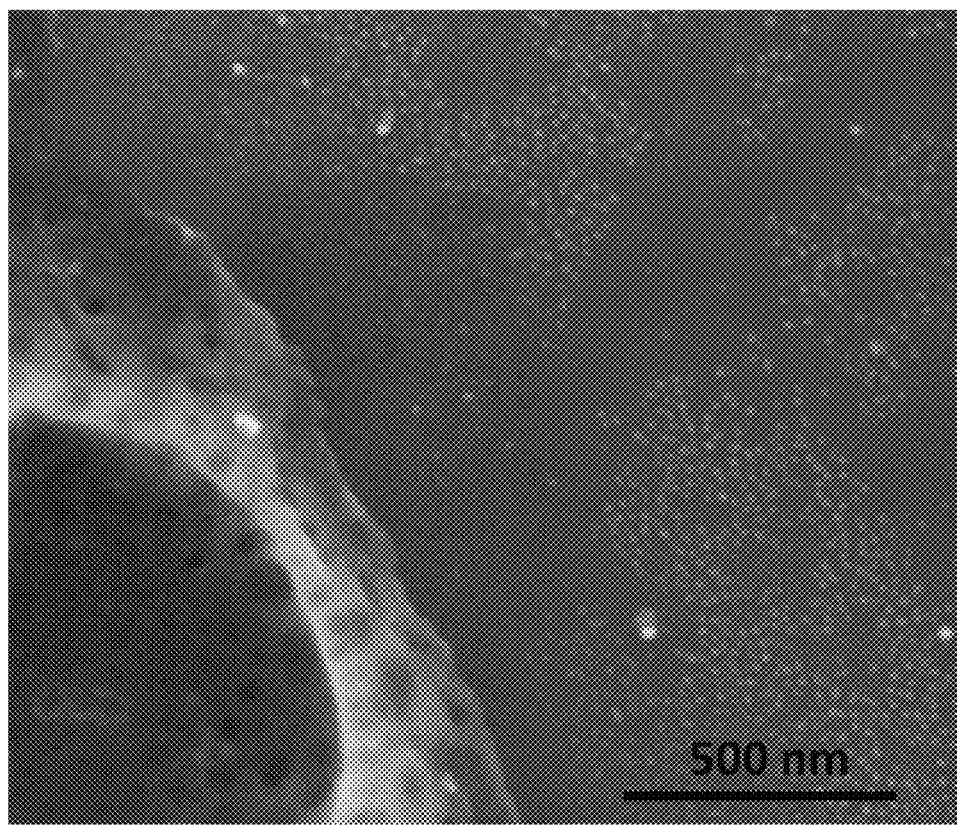
FIGS. 7(a) and 7(b) depict nanopores formed after sintering a deposited structure, with the inset in FIG. 7(b) depicting the surface profile along line 1.
Figure 7B:
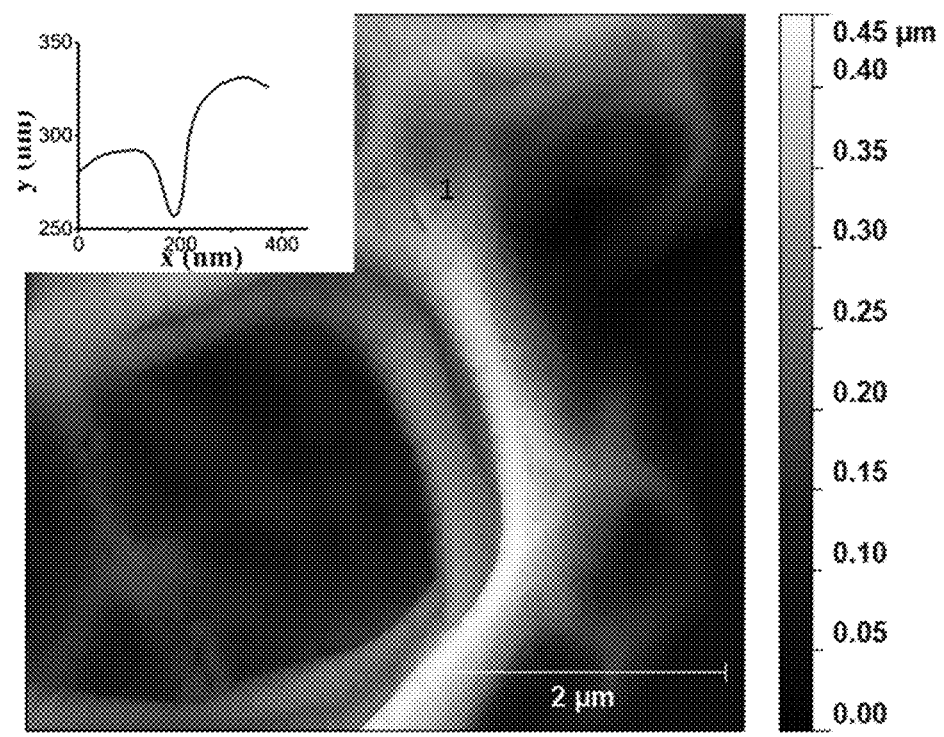
Figure 8:
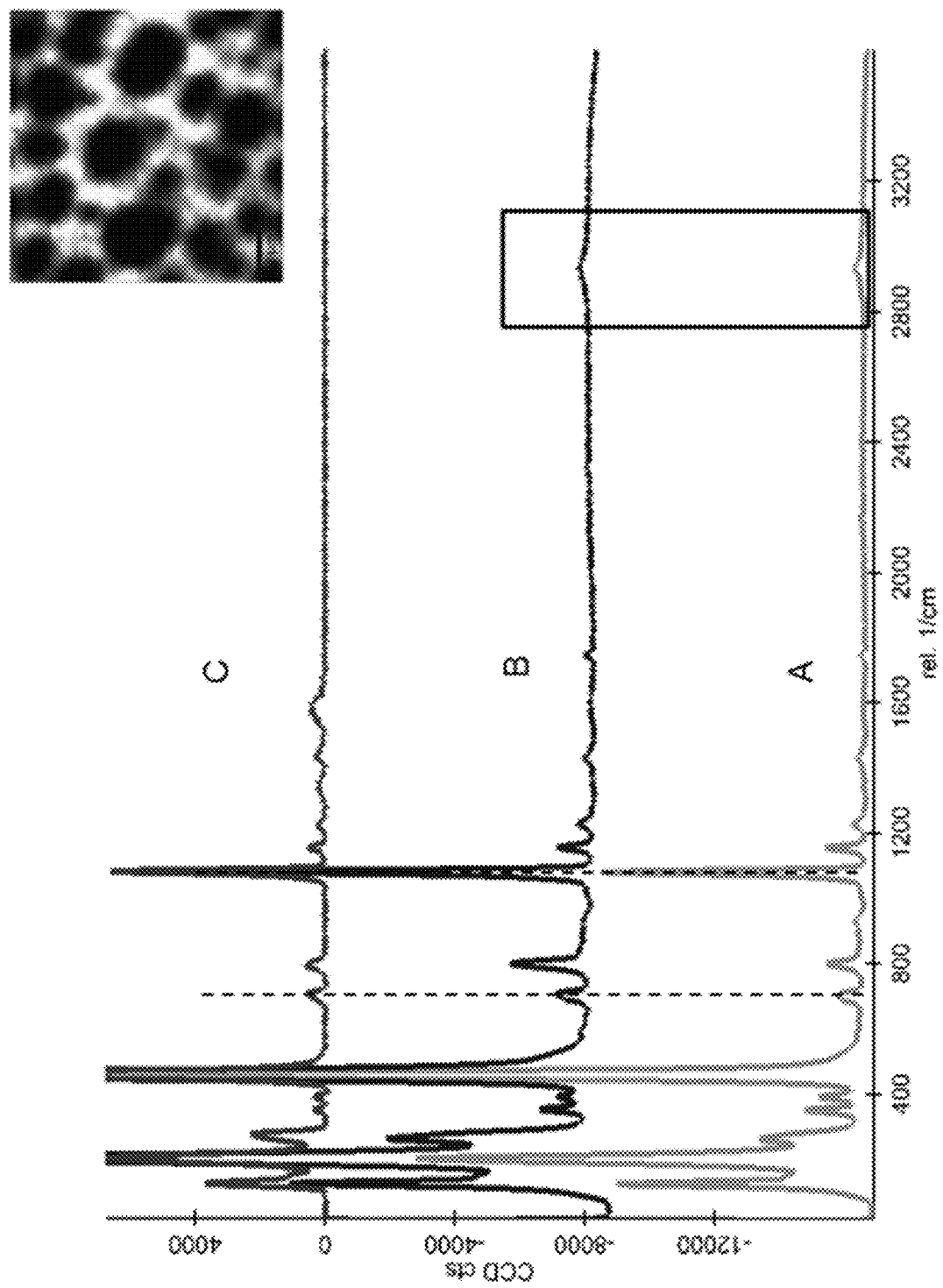
FIG. 8 depicts the Micro-Raman analysis of deposited $CaCO_3$ structures, with the inset being a Confocal Raman spectral image of the structure mapping the intensity of the peak at 1083 $cm^{-1}$.
Figure 9A:
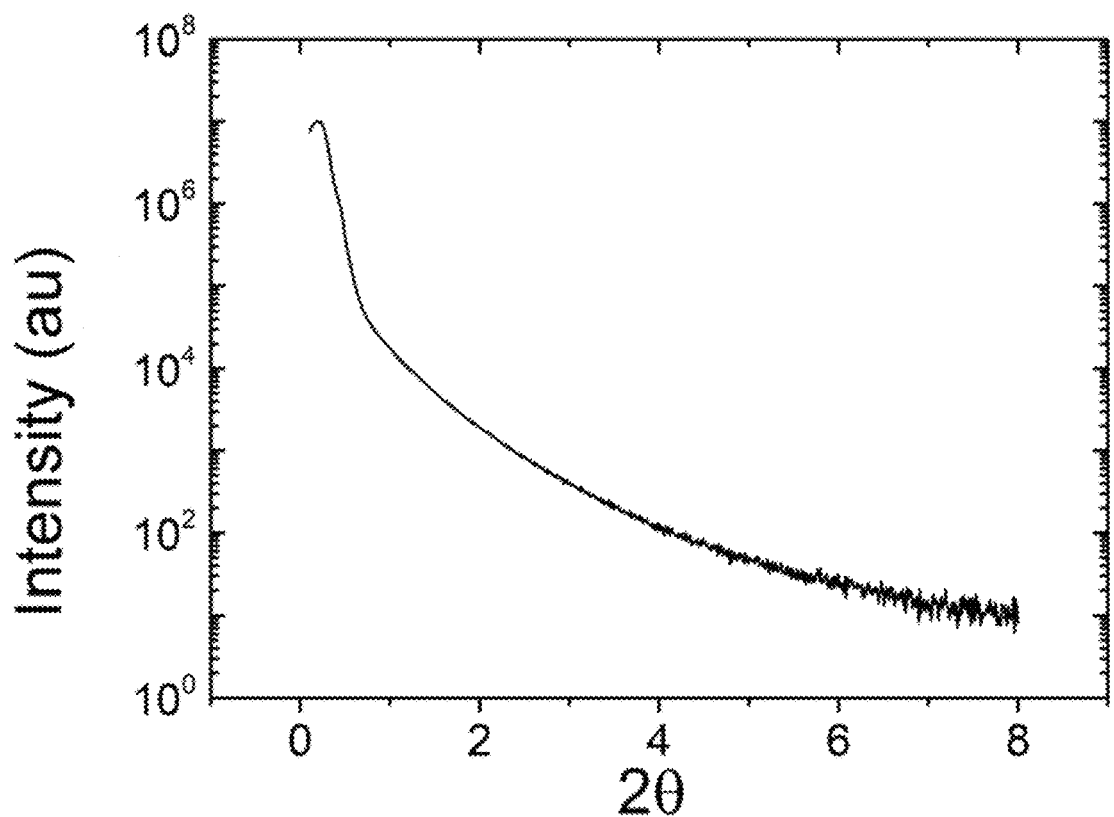
FIGS. 9(a)-(d) are XRD patterns of deposited $CaCO_3$ structures, with the insets in FIGS. 9(b) and 9(d) being images of dynamic water contact angle measurements on deposited $CaCO_3$ structures.
Figure 9B:
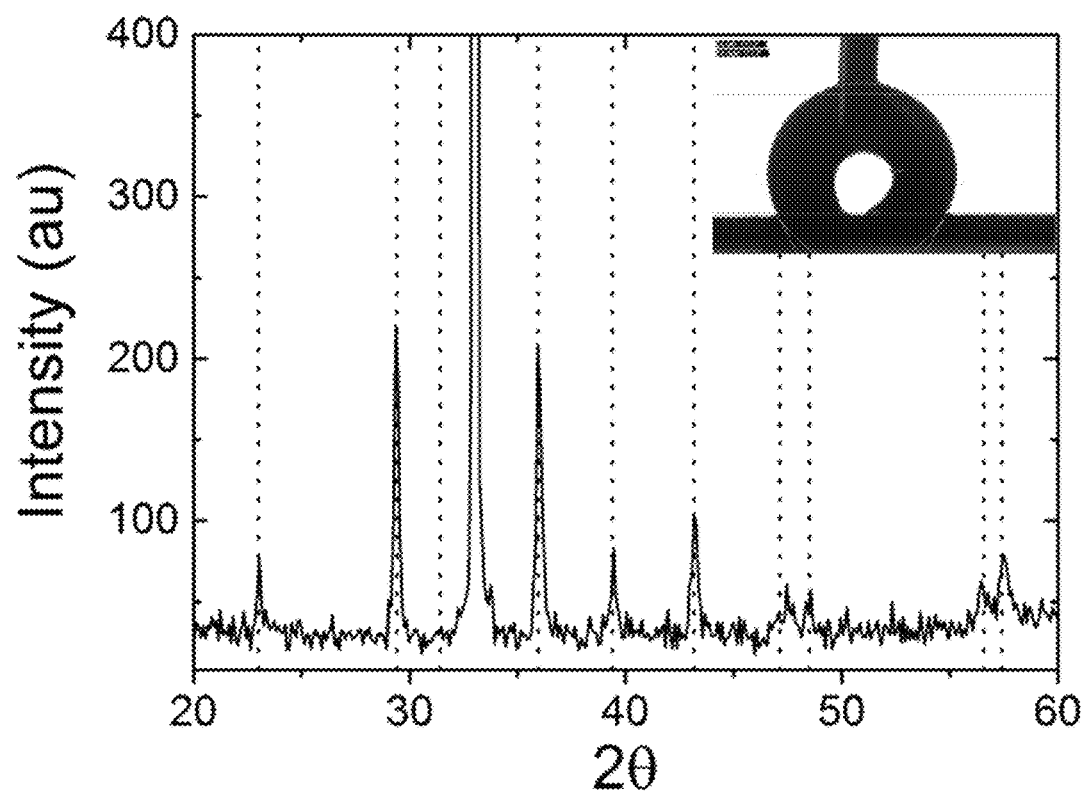
Figure 9C:
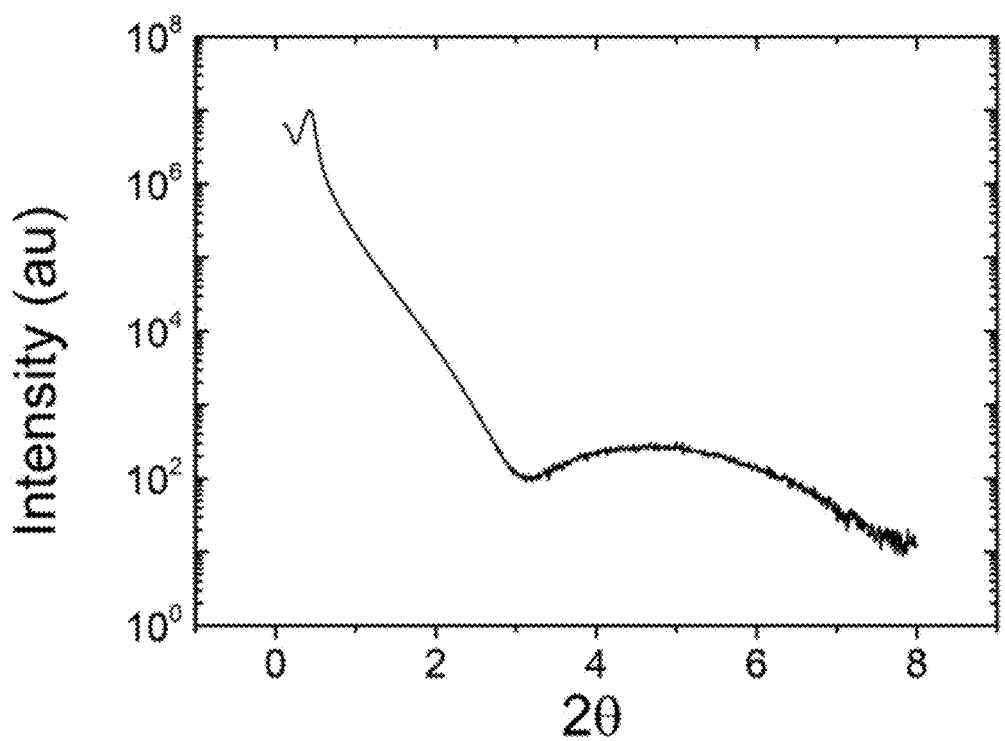
Figure 9D:
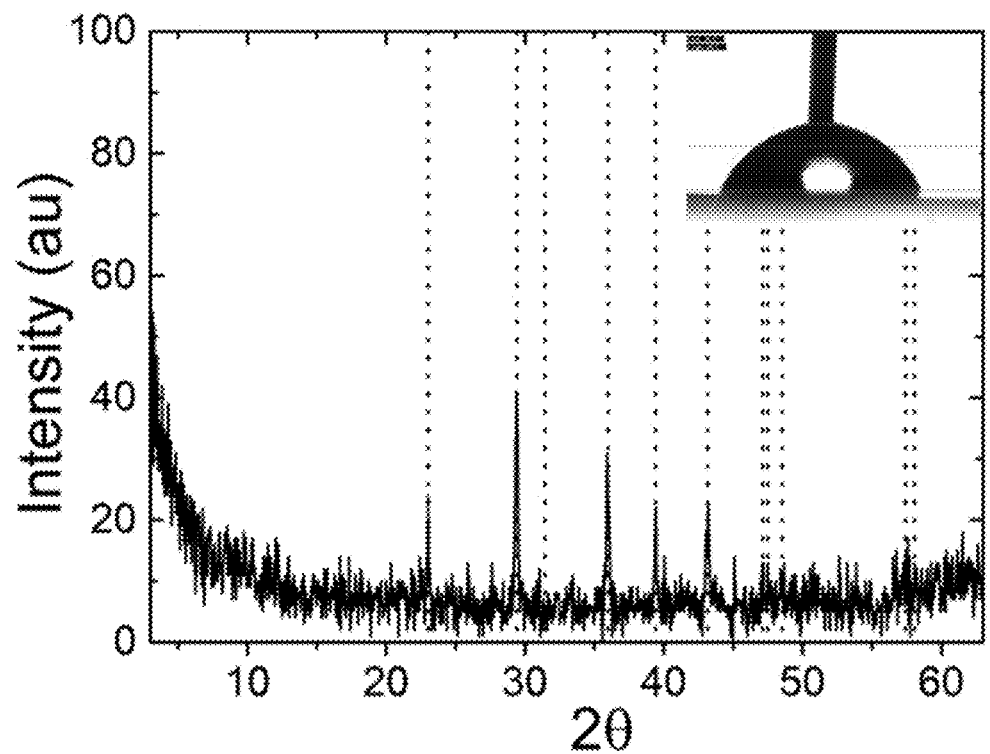
Figure 10A:
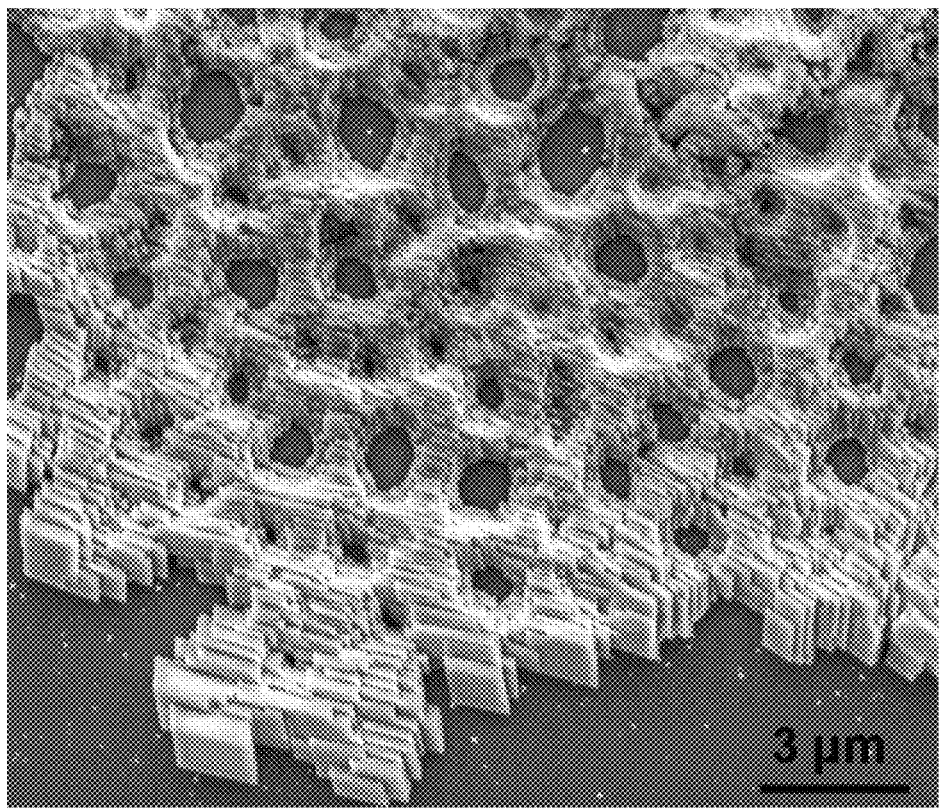
FIGS. 10(a) and 10(b) are SEM images of deposited $CaCO_3$ structures after washing with water.
Figure 10B:
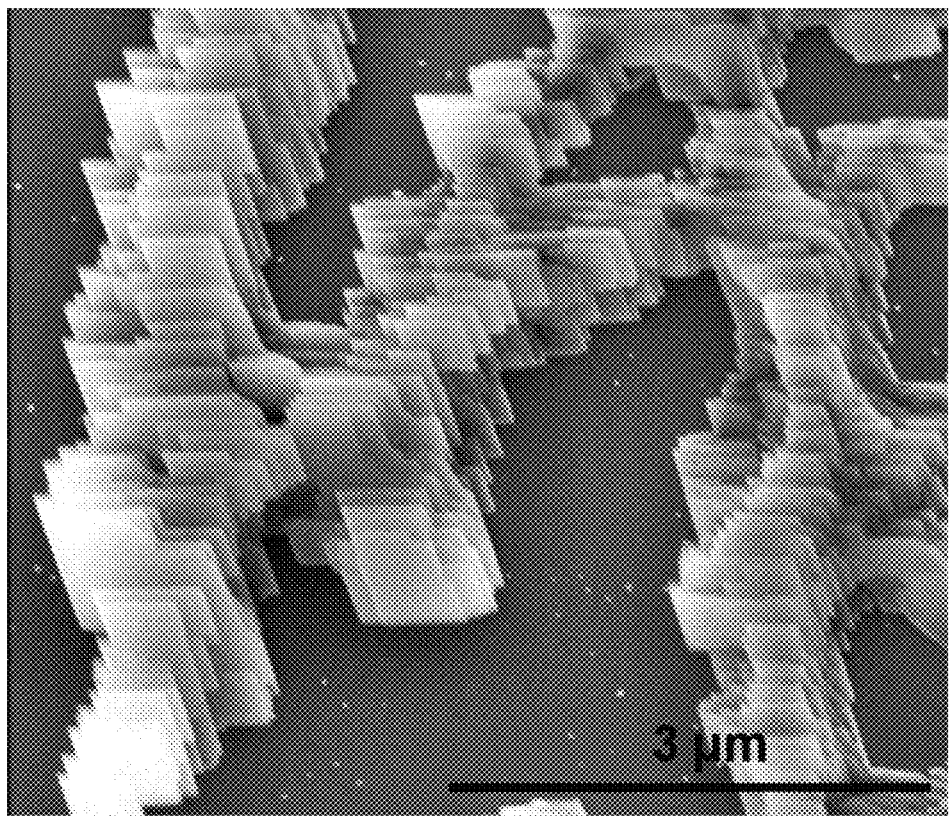
Figure 11A:
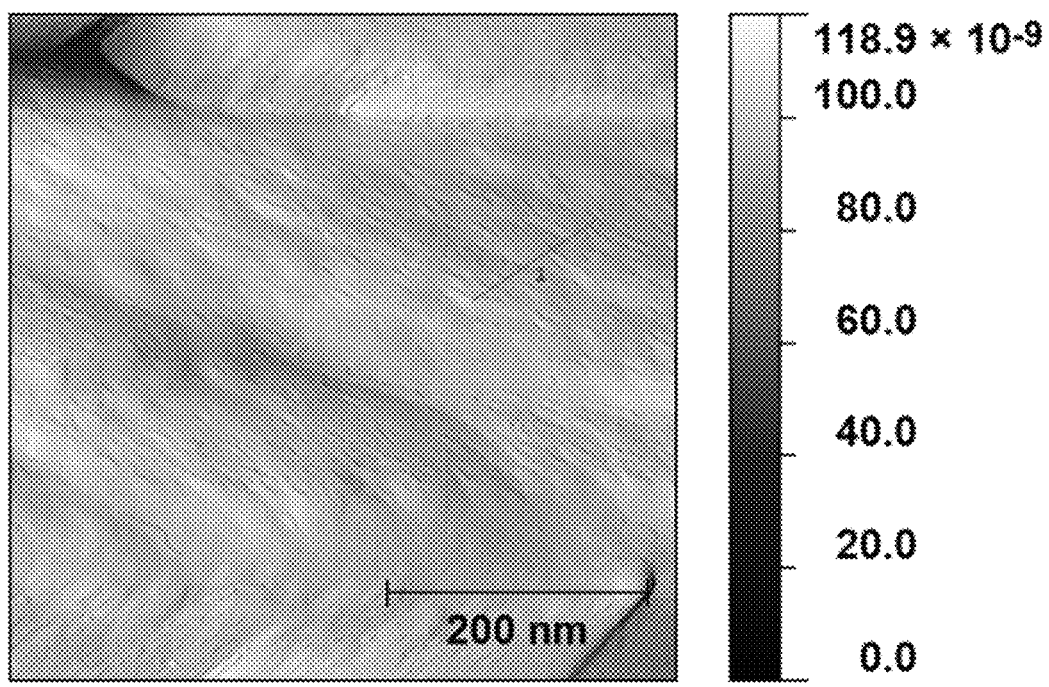
FIGS. 11(a) and 11(c) are AFM images of deposited $CaCO_3$ structures after washing with water.
Figure 11B:
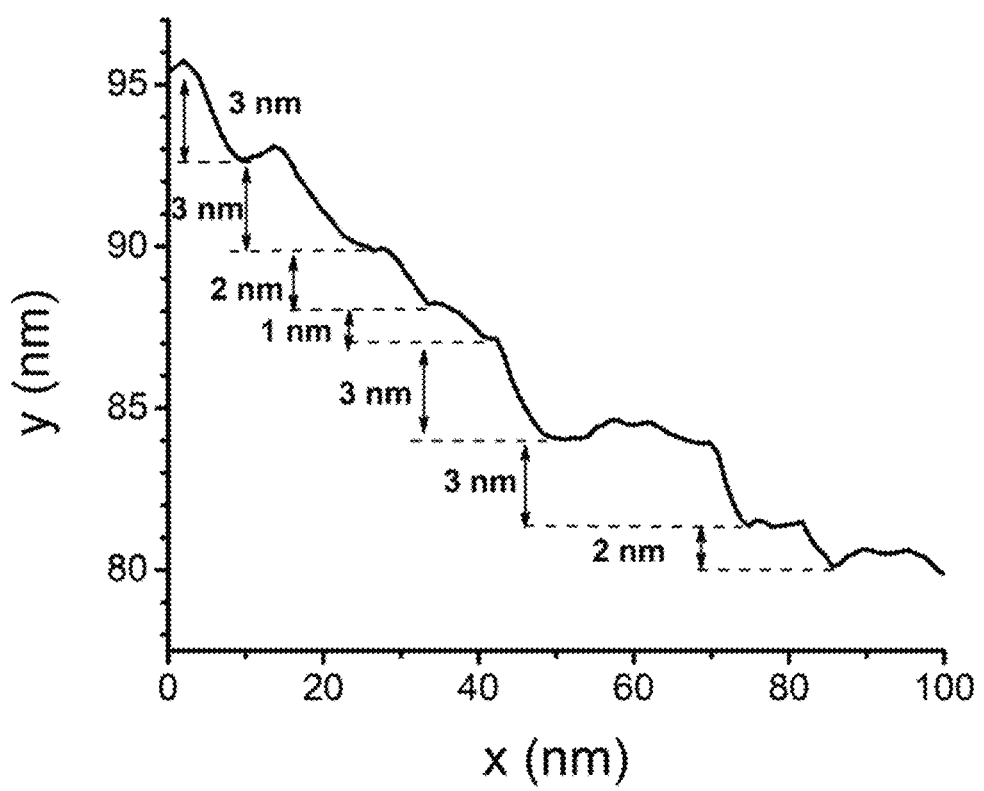
FIG. 11(b) is a surface profile along line 1 in FIG. 11(a).
Figure 11C:
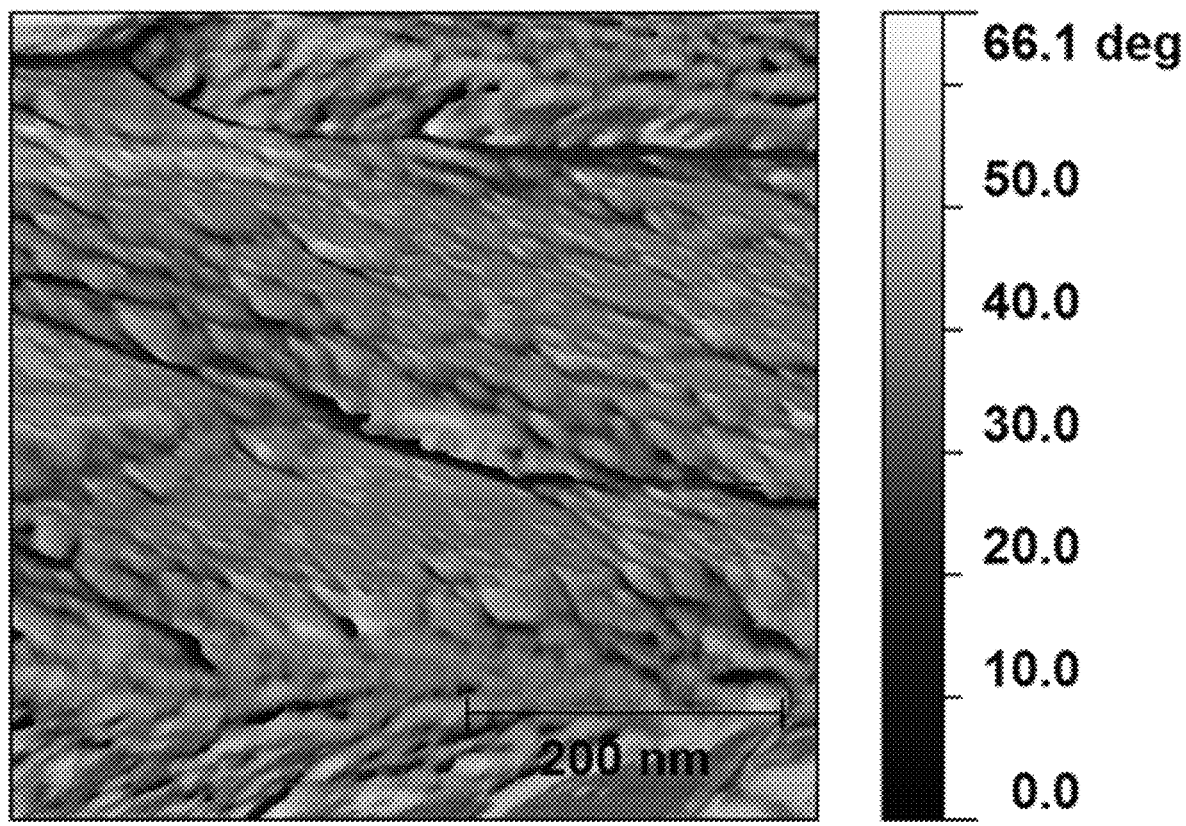
Figure 12:
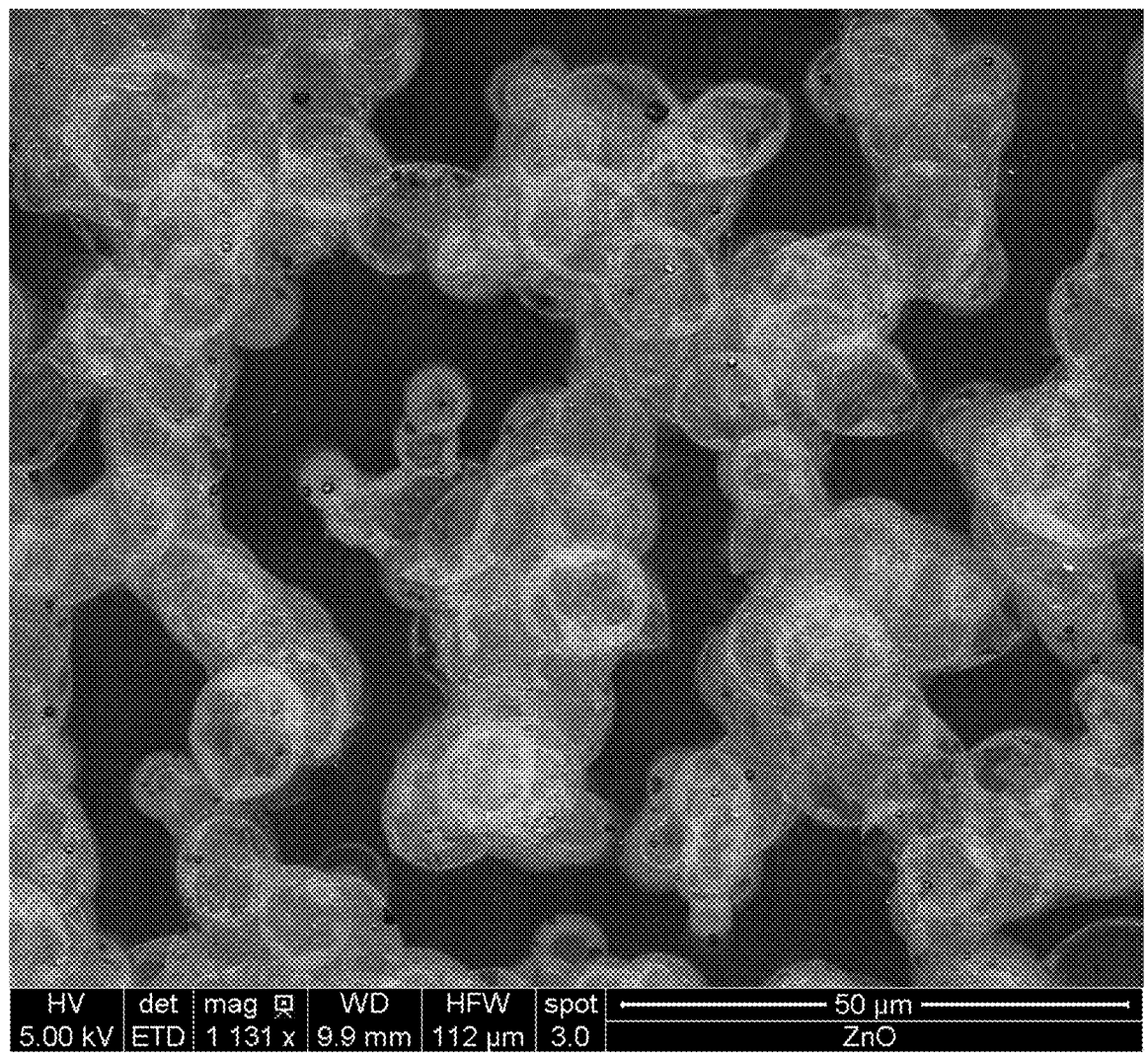
FIG. 12 is an image of zinc oxide structures generated by deposition of water droplets that do not contain $CO_2$ gas.

The observed patterns of nanowires, as shown in FIGS. 1(a), 2(b) and 2(d), were the result of short deposition times of aerosols produced using either the nozzle or the capillary wherein the mass-flow rates are considerably lower than those produced using the 1/16 in stainless steel tubing. Similar patterns were also observed for deposition of the aerosols produced using the 1/16 in stainless steel tubing in the regions of low droplet impact probability. FIG. 5 depicts one such shadowed region where the paths of drying droplets are clearly shown. The droplets may be mobile and move along the surface in the gas flow direction, producing the elongated coffee-rings observed in FIG. 5. A mesh of nanowires may be produced on the surface after a short deposition time.

After the initial formation of nanowires over the surface, a different deposition mechanism may occur. The impacting droplets may be immediately pinned due to the increased roughness of the surface produced by the presence of the nanowires. Considerable on-surface coalescence may be produced as a result of the droplet impact frequency of about 10 kHz to about 100 kHz and the droplet lifetime on the order of about 100 ms. This coalescence may produce the microstructures observed in FIGS. 4(*a*) and 4(*b*). Continued deposition takes place preferentially along the periphery of the droplets, increasing the breadth and height of the walls of the isolated microstructures. After long-term deposition, the isolated microstructures may merge together resulting in the formation of the membrane-like patterns shown in FIGS. 1(*c*), 1(*d*), 2(*a*), 2(*c*), 3(*a*) and 3(*b*). The thickness of the walls of the microstructures increases as the film thickness increases. As the film thickness grows with continued deposition the thermal conductivity of the surface decreases due to the formation of the porous structure, and the kinetics of film growth slow down. According to one embodiment, the deposited film thickness may be less than about 100 nm. According to an alternative embodiment, the deposited film thickness may be about 1 μm to about 3 μm. The thickness growth of $CaCO_3$ scaffolds from 500 nm to 2000 nm over a deposition time of 20 minutes at a temperature of 130° C. and $CO_2$ pressure of 120 bar is shown in FIG. 6.

The presence of dissolved $CO_2$ in the droplets is beneficial for the formation of micron-sized pores. In control experiments, where the aerosols were generated by dispersing dilute solutions of zinc acetate in water using a pharmaceutical nebulizer and deposited on heated silicon substrates at 130° C., patterns of drying spheres were observed instead of porous scaffolds as shown in FIG. 12.

FIG. 7(*a*) shows a typical $CaCO_3$ scaffold with a pore diameter of 1-3 μm produced under optimal process conditions of a pressure of 120 bar, a temperature of 130° C., and a deposition time of 20 minutes. The presence of a secondary structure of nanopores within the $CaCO_3$ scaffolds is also observed. Atomic Force Microscope (AFM) analysis along line 1 in FIG. 7(*b*) confirmed the presence of nanopores with size of about 50 nm, with the inset depicting a surface profile along line 1. The nanopore formation may take place during the sintering step via decomposition of residual $Ca(CH_3COO)_2$ precursor present in the deposited microstructure.

As shown in FIG. 8, Micro-Raman analysis of the non-sintered films A indicates the presence of $CaCO_3$, (band at 1083 $cm^{-1}$, $v_1$ symmetric stretch, $CO_3^{2-}$) formed by the precipitation in carbonated water droplets. However, the presence of residual $Ca(CH_3COO)_2$ precursor in small quantities is also indicated by the band at 2928 $cm^{-1}$ corresponding to C-H stretch, which is not present in the Raman spectrum of sintered films C. The non-sintered films were soaked in water for 30 minutes, and the acetate bands of the Raman spectrum B diminished in intensity in the washed samples as shown in FIG. 8. This result indicates that the acetate components are buried within and protected by the $CaCO_3$ deposits of the microstructure. During sintering, the release of gaseous products may result in the formation of a nanoporous structure. The water contact angle of $CaCO_3$ films may also increase upon sintering due to the formation of nanoscale pores, as shown in the water droplet contact angle tests depicted in the insets of FIGS. 9(*b*) and 9(*d*). The sintering may take place over a period of about 6 hours to about 8 hours.

XRD analysis of the samples indicates that $CaCO_3$ is the majority component of the deposits as shown in FIGS.

9(a)-(d). FIGS. 9(a) and 9(b) depict the XRD patterns of sintered $CaCO_3$ scaffolds. By contrast, FIGS. 9(c) and 9(d) depict the XRD patterns of non-sintered $CaCO_3$ films after immersion in water for 30 minutes. Ostwald ripening may occur when the deposited films are exposed to water, resulting in changes to the morphology of non-sintered films as shown in FIGS. 10(a) and 10(b), where two-dimensional $CaCO_3$ plates or nanosheets one unit cell thick can be seen stacked together. FIGS. 11(a) and 11(c) show AFM images of the stacks. FIG. 11(b) depicts a surface height profile along line 1 in FIG. 11(a), indicating that the step sizes between plates are about 1 nm to about 3 nm. The $CaCO_3$ nanosheets were well aligned and single crystalline, with a nominal thickness of approximately 17 Å.

The crystal structure of the $CaCO_3$ scaffolds was characterized by X-ray diffraction as shown in FIGS. 9(a)-(d), confirming the presence of the calcite phase of $CaCO_3$ (JCPDS 005-0586). In contrast to previous studies the investigated $CaCO_3$ scaffolds show an intensity of the {110} texture of calcite films which is five times stronger than observed for standard calcite powder XRD, which is reported to be dominated by the {104} texture. The presence of various textures may be influenced by organic additives and the process of precipitation.

Commercially available chemical reagents were employed. Precursor materials such as calcium acetate hydrate $(Ca(CH_3COOH)_2).H_2O)$, zinc acetate, cobalt acetate, silver acetate, copper acetate, and gold chloride were purchased at the highest purity grade (99.99%) from Sigma Aldrich. $CO_2$ liquid was purchased from Air Products Middle East FZE (Dubai-UAE). The water used in all experiments was prepared in a three-stage Millipore MilliQ plus 185 purification system and had a resistivity of 18.2 mΩcm.

Figure 13:
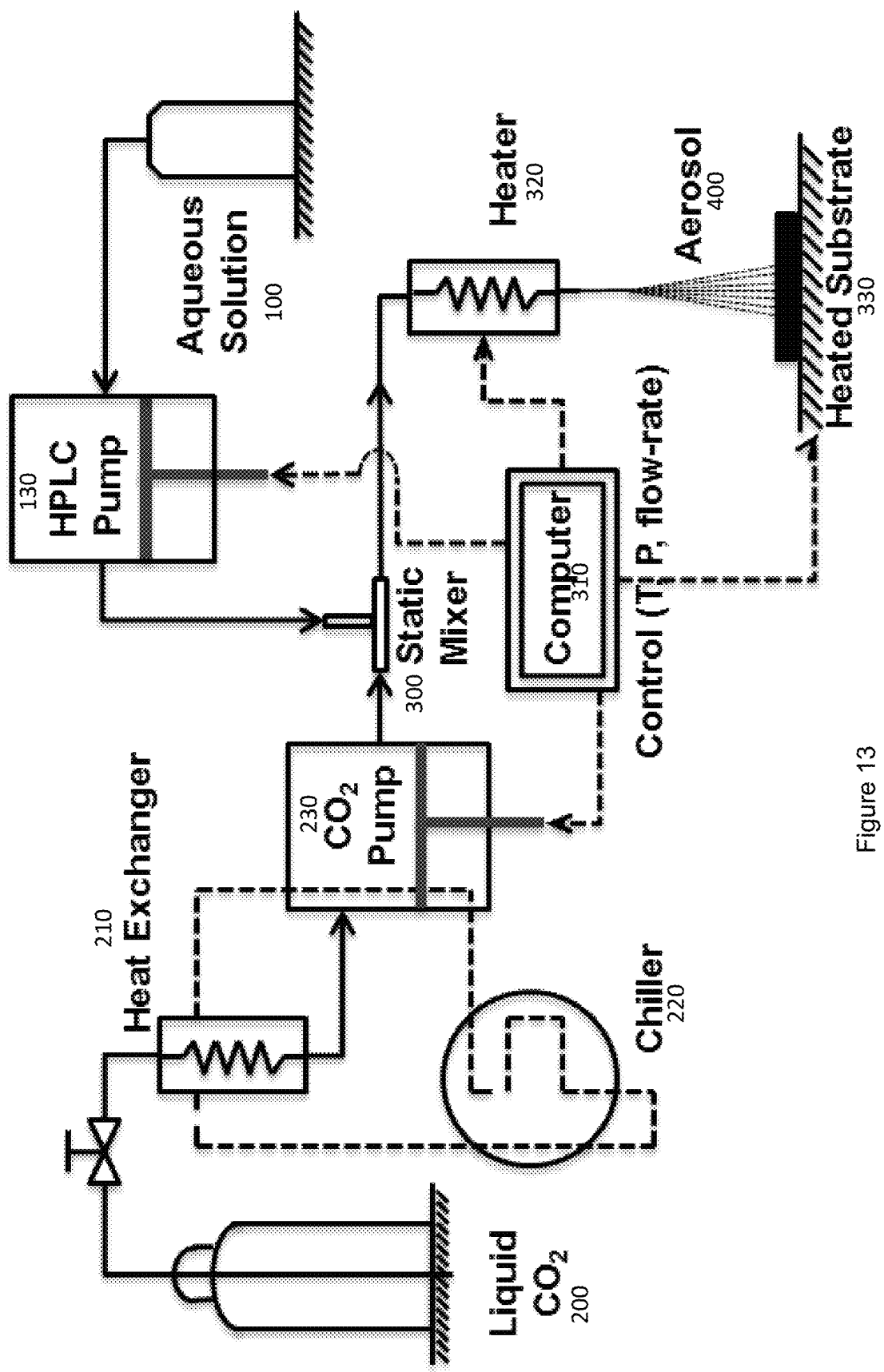
FIG. 13 is a schematic diagram of device for the production of an aerosol of water droplets containing $CO_2$ gas.

The process flow diagram for producing the aerosol is depicted in FIG. 13. The $CO_2$ may be supplied in liquid form from a storage tank 200 to a heat exchanger 210 coupled to a chiller 220. The flow rate of sc-$CO_2$ was adjusted to maintain a constant pressure, and the aqueous solution was pumped at a constant mass flow rate. A $CO_2$ pump 230 may be utilized to pressurize the $CO_2$ before being supplied to a static mixing device 300. A range of experiments were carried out initially to establish the operating space in terms of pressure, temperatures, flow rates, capillary dimensions and spray tip location. The process was designed to mix two streams, particularly sc-$CO_2$ and an aqueous solution, at constant pressure and temperature in a static mixer. The static mixing device 300 mixes the $CO_2$ with an aqueous solution that is provided to the static mixing device from an aqueous solution storage tank 100 by an aqueous solution pump 130. Once mixed, the solution streams were depressurized either through a 2 inch long, 1/16 inch inner diameter (ID) stainless steel (S.S.) tubing or a 1 inch long, 125 μm diameter stainless steel capillary tube or a sapphire nozzle with a 125 μm diameter. The mixture of the $CO_2$ and the aqueous solution may pass through a heater 320 before being depressurized to form an aerosol 400. The aerosol 400 may be collected on a heated substrate 330. A computer 310 may be configured to control the $CO_2$ pump 230, aqueous solution pump 130, heater 320 and heated substrate 330 to produce the desired conditions, such as temperature, pressure and flow rate. According to another embodiment, the coating apparatus may include an array of spray nozzles to deposit a coating on a substrate in the form of a wide-format, roll-to-roll moving surfaces.

According to another embodiment, the aerosol may be produced by any other suitable process. For example, the aerosol may be produced by an inkjet process. Inkjet processes provide the benefit of reduced cost and wide availability. Additionally, an inkjet process may be utilized to produce an aerosol without the aid of supercritical $CO_2$.

A transport table was installed underneath the spray on which an aluminum heating block was mounted. The heating block was raised or lowered to adjust the spray distance. The substrate temperature was controlled by adjusting the heat input to the aluminum block. The mounting block included screws at its corners to hold 2 inch×2 inch substrates, such as silicon and quartz, to be coated by the depressurized aerosol spray. The translational table was capable of moving the substrate under the spray at a predetermined rate, such as 0.5 inch/sec.

The following general experimental conditions were employed. A flow rate of 0.1 wt % solute ranged from 1-4 g/minute. Sc-$CO_2$ was used to adjust the pressure in the mixer in the range of 65-130 bar. The mixing chamber temperature was maintained at 100° C. The sc-$CO_2$ line temperature to the mixing chamber was maintained at 100° C. A 2 inch×2 inch silicon wafer mounted to the heated aluminum block on the translation table was utilized as a substrate.

Alternative experiments were carried out with quartz and sapphire wafers as substrates. The temperature of the aluminum block was controlled throughout the experiment in the range of 80° C. to 200° C. The tip of the 1/16 inch S.S. tubing was mounted at either 1 inch or 2 inches above the silicon substrate which was moved back and forth (cycled) at 0.5 inch/second. The coating time was up to about 20 minutes. In all cases, the samples were post treated at a higher temperature of 450° C. for at least 3 hours.

Surface morphology of the thin films was characterized by field emission scanning electron microscopy (FE-SEM) and by Atomic force microscopy (AFM) in tapping mode. Height, phase and amplitude images were acquired simultaneously. Cantilevers with a frequency of 204-497 kHz and a force constant of 10-130 N/m were employed. The set point ratio was kept at 0.9.

X-ray measurements were made on an Panalytical Empyrean X-ray diffractometer using a Cu anode. The X-rays were focused using a parallel mirror fitted with 0.02 rad Soller slits and a 1/32° divergent slit on the sample. The sample was aligned for X-ray reflectivity, the substrate was parallel to the X-ray beam and blocking one-half of the incident intensity. The diffracted X-rays passed through a 0.27° parallel plate collimator and 0.02 rad Soller slits to a proportional detector. The measurements were made with consistent step sizes and times per step.

Optical and Raman microscopy was performed on a WiTec alpha confocal Raman microscope equipped with a 50× and 100× objectives. The pinhole diameter of the confocal microscope was kept constant at 100 Raman spectra were acquired using a 532 nm laser for excitation (12 mW power) and recorded using a CCD camera maintained at −60° C. The integration time for the acquisition of spectra was kept constant at 3 seconds. Each spectrum depicted was an average of 10 consecutive scans. The films were rescanned after initial data acquisition to detect any radiation-induced damage. No chemical change in the film composition was detected for an exposure time of 30 seconds at 12 mW power.

Dynamic water contact angle measurements were carried out by using an SCA-20 from Data Physics at room temperature, as depicted in the insets of FIGS. 9(b) and 9(d). The thickness of calcinated $CaCO_3$ scaffolds were measured by using a Dektak XT. Height profiles were collected from scratches made on the scaffold. The resulting profiles were analyzed by Vision64™ software. The measurements were repeated at least three times.

A $CaCO_3$ coating was applied to titanium dental implants for the purposes of preclinical model testing. A total of 24 grade II (commercially pure) titanium alloy implants were obtained from a medical device manufacturer (Emfil, Itu, Sao Paulo). These devices were screw shaped and presented 4 mm in diameter and 10 mm in length. Half of the implants were coated with $CaCO_3$ through the methodology presented above and the other half remained uncoated as a control group. Following the coating process, the implants were γ radiation sterilized.

The preclinical laboratory in vivo model selected was the sheep, with n being 6 animals. The study was approved by the Ethics Committee for Animal Research at the Ecole Nationale Veterinaire d'Alfort (protocol number 13-011; 14/05/13-3 -Maisons-Alfort, Val-de-Marne, France). The Finnish Dorset crossed-bred sheep selected were approximately 1.5 years old and each weighed approximately 150 pounds. The sheep remained in the facility for 2 weeks prior to the surgical procedures to place the implants. A total of 24 implants were distributed among 2 experimental groups, with n being 6 per group and time-point, and four per animal. The pelvis access to place the implants was performed by an antero-posterior incision of 15 cm in length, which was followed by bunt dissection of the fat and muscle layers. The implants were placed sequentially from proximal to distal at a distance of 2 cm from the first implant's center at the central region of the bone. On each sheep, 2 implants were first placed in one side of the hip, and after 5 weeks, the other side of the hip underwent the same procedure for a total of 4 implants per animal. One week later the animals were sacrificed and thus each animal provided samples that remained in vivo for 1 and 6 weeks. All surgeries were conducted under general anesthesia.

No clinical signs of inflammation were observed immediately following surgery or throughout the course of the experiment. No postoperative complications were detected, and no implant was excluded from the study because of clinical instability immediately after euthanasia.

Following sacrifice of the sheep, the implants in bone were reduced to blocks and processed for nondecalcified histologic sections. The 30 μm sections were Stevenel's Blue Von Gieson's fuchsin acid stained and referred to histometric measurement of the Bone Area Fraction Occupancy (BAFO) of the region between implant threads performed by commercially available computer software (ImageJ). The statistical evaluation of the effects of time and implant surface on BAFO measurements was performed by a Wilcoxon sign rank test. Statistical significance was set at 5% (α=0.05).

As shown in FIGS. 14(a)-d), histologic observation of optical micrographs indicated bone formation in close contact to the implant for all groups at both time-points, demonstrating that both coated and uncoated implant surfaces were biocompatible and osseoconductive. It was evident that the amount of bone between implant threads substantially increased from 1 to 6 weeks in vivo for both groups. Although no qualitative differences in bone amount were measurable at 1 week in vivo, the amount of bone appeared higher at 6 weeks for the $CaCO_3$ group compared to the uncoated surface, as demonstrated by comparing FIGS. 14(c) and (d). From a quantitative standpoint, a significant increase in BAFO was observed from 1 to 6 weeks in vivo (p<0.001). This increase was expected for both implant groups as early bone healing progressed around the implants. As shown in FIG. 14(e), the mean BAFO percentage results at 1 week exhibited no significant differences between groups. This result was expected due to the short implantation time in vivo, where primarily osteogenic connective tissue formation occurred in proximity with the implant surfaces with very little new bone formation. At 6 weeks, the $CaCO_3$ group presented significantly higher (p<0.02) BAFO than the uncoated group, demonstrating that the improved osseoconductive properties associated with the $CaCO_3$ coated implants produced higher amounts of new bone growth. The improved osseoconductive properties may be due at least in part to the intimate relationship between the surface and the host biofluids immediately after implantation, the increased biocompatible nature of its structure due to its composition, and hastened bone healing as a result of the release of bioactive ceramic ionic components in vivo, each of which is contributed to by the $CaCO_3$ coating. The in vivo results demonstrate that the $CaCO_3$ coating hastened bone formation around the titanium implant.

Additional Notes

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." Any ranges cited herein are inclusive.

The terms "substantially" and "about" used throughout this Specification are used to describe and account for small fluctuations. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed:

1. A process comprising:

mixing a stream of supercritical $CO_2$ with an aqueous solution of an organic salt in a continuous flow operation;

creating an aerosol from the mixture; and depositing the aerosol on heated substrates having a temperature of 80° C. to 150° C.

2. The process of claim 1, further comprising sintering the deposited aerosol.

3. The process of claim 2, wherein the sintering produces a nanowire mesh or a hierarchically porous structure.

4. The process of claim 2, wherein the sintering is at a temperature of at least 300° C. for 6 hours to 8 hours.

5. The process of claim 1, wherein the supercritical $CO_2$ is at a pressure of 0.1 MPa to 0.3 MPa.

6. The process of claim 1, wherein creating the aerosol comprises rapidly expanding the mixture through a capillary, nozzle, or tube.

7. The process according to claim 1, wherein the organic salt is described by the formula:

$$M_x(N)_y$$

wherein M is at least one of Ca, Ag, Cu, Zn, Co, Fe, Mn, and Ni, and N is at least one of acetate ($CH_3COO^-$), acetylacetonate ($CH_3COCH_2COO^-$), and oxalate ($C_2O_4^{2-}$.

8. The process according to claim 1, wherein the deposited material comprises nanowires.

9. The process according to claim 1, wherein the deposited material has a thickness of less than 100 nm.

10. The process according to claim 1, wherein the deposited material comprises microporous inorganic membranes.

11. The process according to claim 1, wherein the deposited material has a thickness of 1 μm to 3 μm.

12. The process according to claim 1, wherein the deposited material comprises:

nanopores with an average diameter of less than 100 nm, and pores with an average diameter of greater than 100 nm.

13. The process according to claim 1, wherein the deposited material comprises $CaCO_3$.

14. The process according to claim 1, wherein the substrate comprises titanium.

15. The process according to claim 1, wherein the substrate comprises a medical implant.

16. A process comprising:

creating an aerosol from an aqueous solution of an organic salt in a continuous flow operation, the organic salt is described by the formula $M_x(N)_y$ wherein M is at least one of Ca, Ag, Cu, Zn, Co, Fe, Mn, and Ni, and N is at least one of acetate ($CH_3COO^-$), acetylacetonate ($CH_3COCH_2COO^-$), and oxalate ($C_2O_4^{2-}$; and depositing the aerosol on heated substrates, wherein creating the aerosol comprises an inkjet process.

* * * * *